(12) United States Patent
Hunt et al.

(10) Patent No.: US 8,197,512 B1
(45) Date of Patent: Jun. 12, 2012

(54) SYSTEM AND METHOD FOR SPINE STABILIZATION USING RESILIENT INSERTS

(75) Inventors: Wesley Hunt, Austin, TX (US); H. Kim Le, Houston, TX (US); Alex Chang, Lake Jackson, TX (US); Anwaar Qadir, Cleveland, TX (US)

(73) Assignee: Zimmer Spine, Inc., Minneapolis, MN (US)

( * ) Notice: Subject to any disclaimer, the term of this patent is extended or adjusted under 35 U.S.C. 154(b) by 908 days.

(21) Appl. No.: 12/174,484

(22) Filed: Jul. 16, 2008

(51) Int. Cl.
*A61B 17/70* (2006.01)
(52) U.S. Cl. ....................................... 606/246
(58) Field of Classification Search .............. 606/60, 606/246–279, 287, 65, 300; 403/76, 77
See application file for complete search history.

(56) References Cited

U.S. PATENT DOCUMENTS

| | | | |
|---|---|---|---|
| 4,433,677 A | 2/1984 | Ulrich et al. | |
| 4,773,402 A | 9/1988 | Asher et al. | |
| 5,282,863 A * | 2/1994 | Burton | 606/254 |
| 5,443,467 A * | 8/1995 | Biedermann et al. | 606/65 |
| 5,549,608 A * | 8/1996 | Errico et al. | 606/264 |
| 5,683,392 A | 11/1997 | Richelsoph et al. | |
| 5,702,393 A * | 12/1997 | Pfaifer | 606/328 |
| 5,728,098 A * | 3/1998 | Sherman et al. | 606/269 |
| 5,954,725 A * | 9/1999 | Sherman et al. | 606/78 |
| 5,964,760 A * | 10/1999 | Richelsoph | 606/279 |
| 5,989,250 A | 11/1999 | Wagner et al. | |
| 5,997,539 A * | 12/1999 | Errico et al. | 606/278 |
| 6,010,503 A * | 1/2000 | Richelsoph et al. | 606/278 |
| 6,074,391 A * | 6/2000 | Metz-Stavenhagen et al. | 606/278 |
| 6,132,430 A * | 10/2000 | Wagner | 606/264 |
| 6,132,432 A * | 10/2000 | Richelsoph | 606/278 |
| 6,132,434 A * | 10/2000 | Sherman et al. | 606/78 |
| 6,171,311 B1 * | 1/2001 | Richelsoph | 606/252 |
| 6,187,005 B1 * | 2/2001 | Brace et al. | 606/264 |
| 6,248,105 B1 * | 6/2001 | Schlapfer et al. | 606/266 |
| 6,355,040 B1 * | 3/2002 | Richelsoph et al. | 606/272 |
| 6,416,515 B1 * | 7/2002 | Wagner | 606/250 |

(Continued)

FOREIGN PATENT DOCUMENTS

WO WO 2008013539 A2 1/2008

OTHER PUBLICATIONS

Office Action issued in U.S. Appl. No. 12/167,798, mailed May 31, 2011, 7 pages.

(Continued)

*Primary Examiner* — Alvin J Stewart
(74) *Attorney, Agent, or Firm* — Seager Tufte & Wickhem LLC

(57) ABSTRACT

An apparatus for anchoring a rod to a bone fastener in a spine stabilization system. A first resilient insert may have two deflectable arms and a first channel formed therein. A second resilient insert may have two deflectable arms and a second channel formed therein. A cylindrical body may have a passage, wherein the first resilient insert and the second resilient insert have a width greater than the inner diameter of the cylindrical body when the first resilient insert is in a neutral state. Advancement of the first resilient insert or the second resilient insert into the passage deflects the two deflectable arms inward, causing the width of the first or second channel to decrease, and inhibiting the first resilient insert or the second resilient insert from moving relative to the cylindrical body.

20 Claims, 6 Drawing Sheets

U.S. PATENT DOCUMENTS

| | | |
|---|---|---|
| 6,454,773 B1 * 9/2002 | Sherman et al. | 606/78 |
| 6,485,491 B1 * 11/2002 | Farris et al. | 606/250 |
| 6,488,681 B2 * 12/2002 | Martin et al. | 606/278 |
| 6,562,040 B1 * 5/2003 | Wagner | 606/264 |
| 6,565,566 B1 * 5/2003 | Wagner et al. | 606/267 |
| 6,565,567 B1 * 5/2003 | Haider | 606/266 |
| 6,595,992 B1 * 7/2003 | Wagner et al. | 606/250 |
| 6,613,050 B1 * 9/2003 | Wagner et al. | 606/250 |
| 6,660,005 B2 * 12/2003 | Toyama et al. | 606/308 |
| 6,783,528 B2 * 8/2004 | Vincent-Prestigiacomo | 606/246 |
| 6,837,889 B2 * 1/2005 | Shluzas | 606/270 |
| 6,843,791 B2 1/2005 | Serhan | |
| 6,866,664 B2 * 3/2005 | Schär et al. | 606/252 |
| 6,918,911 B2 * 7/2005 | Biedermann et al. | 606/267 |
| 7,022,122 B2 * 4/2006 | Amrein et al. | 606/266 |
| 7,066,937 B2 * 6/2006 | Shluzas | 606/86 A |
| 7,090,674 B2 * 8/2006 | Doubler et al. | 606/277 |
| 7,104,993 B2 9/2006 | Baynham et al. | |
| 7,276,069 B2 * 10/2007 | Biedermann et al. | 606/250 |
| 7,303,563 B2 * 12/2007 | Poyner et al. | 606/279 |
| 7,320,555 B2 * 1/2008 | Chang et al. | 403/122 |
| 7,322,982 B2 * 1/2008 | Vincent-Prestigiacomo | 606/246 |
| 7,335,202 B2 2/2008 | Matthis et al. | 606/266 |
| 7,445,627 B2 * 11/2008 | Hawkes et al. | 606/269 |
| 7,585,299 B2 * 9/2009 | Rezach | 606/60 |
| 7,585,314 B2 * 9/2009 | Taylor et al. | 606/250 |
| 7,585,315 B2 * 9/2009 | Donath | 606/269 |
| 7,678,112 B2 * 3/2010 | Rezach | 606/60 |
| 7,678,139 B2 * 3/2010 | Garamszegi et al. | 606/328 |
| 7,686,835 B2 * 3/2010 | Warnick | 606/264 |
| 7,766,915 B2 * 8/2010 | Jackson | 606/86 A |
| 7,776,067 B2 * 8/2010 | Jackson | 606/246 |
| 7,819,899 B2 * 10/2010 | Lancial | 606/246 |
| 7,828,829 B2 * 11/2010 | Ensign | 606/305 |
| 7,833,248 B2 * 11/2010 | Markworth et al. | 606/253 |
| 7,857,834 B2 * 12/2010 | Boschert | 606/269 |
| 7,862,594 B2 * 1/2011 | Abdelgany | 606/266 |
| 7,892,259 B2 * 2/2011 | Biedermann et al. | 606/264 |
| 7,892,263 B2 2/2011 | Perez-Cruet et al. | |
| 7,935,135 B2 * 5/2011 | Mujwid | 606/266 |
| 7,942,909 B2 * 5/2011 | Hammill et al. | 606/267 |
| 7,947,065 B2 * 5/2011 | Hammill et al. | 606/267 |
| 7,967,850 B2 * 6/2011 | Jackson | 606/301 |
| 8,016,866 B2 * 9/2011 | Warnick | 606/305 |
| RE42,867 E * 10/2011 | Hammill et al. | 606/277 |
| 8,057,515 B2 * 11/2011 | Flynn et al. | 606/246 |
| 8,057,517 B2 * 11/2011 | Flynn et al. | 606/257 |
| 8,062,340 B2 * 11/2011 | Berrevoets et al. | 606/270 |
| 8,075,603 B2 * 12/2011 | Hammill et al. | 606/308 |
| 8,100,946 B2 * 1/2012 | Strausbaugh et al. | 606/266 |
| 8,100,947 B2 * 1/2012 | Ensign et al. | 606/267 |
| 8,100,948 B2 * 1/2012 | Ensign et al. | 606/267 |
| 2002/0035366 A1 * 3/2002 | Walder et al. | 606/61 |
| 2003/0028192 A1 * 2/2003 | Schar et al. | 606/61 |
| 2003/0125742 A1 7/2003 | Yuan et al. | |
| 2003/0167058 A1 * 9/2003 | Shluzas | 606/61 |
| 2004/0138660 A1 7/2004 | Serhan | |
| 2005/0027292 A1 * 2/2005 | Bernard et al. | 606/61 |
| 2005/0080419 A1 * 4/2005 | Donath | 606/61 |
| 2005/0085812 A1 * 4/2005 | Sherman et al. | 606/61 |
| 2005/0096659 A1 * 5/2005 | Freudiger | 606/73 |
| 2005/0154391 A1 * 7/2005 | Doherty et al. | 606/61 |
| 2005/0177156 A1 * 8/2005 | Timm et al. | 606/61 |
| 2005/0192573 A1 * 9/2005 | Abdelgany et al. | 606/61 |
| 2005/0203515 A1 * 9/2005 | Doherty et al. | 606/61 |
| 2005/0216003 A1 * 9/2005 | Biedermann et al. | 606/61 |
| 2005/0240265 A1 10/2005 | Kuiper et al. | |
| 2005/0240266 A1 10/2005 | Kuiper et al. | |
| 2005/0261770 A1 11/2005 | Kuiper et al. | |
| 2005/0273099 A1 * 12/2005 | Baccelli et al. | 606/61 |
| 2005/0277919 A1 * 12/2005 | Slivka et al. | 606/61 |
| 2005/0277923 A1 * 12/2005 | Sweeney | 606/61 |
| 2005/0277924 A1 12/2005 | Roychowdhury | |
| 2005/0277927 A1 * 12/2005 | Guenther et al. | 606/61 |
| 2005/0277928 A1 * 12/2005 | Boschert | 606/61 |
| 2005/0283157 A1 * 12/2005 | Coates et al. | 606/73 |
| 2006/0025767 A1 * 2/2006 | Khalili | 606/61 |
| 2006/0025768 A1 * 2/2006 | Iott et al. | 606/61 |
| 2006/0036244 A1 2/2006 | Spitler et al. | |
| 2006/0079894 A1 4/2006 | Colleran et al. | |
| 2006/0089644 A1 * 4/2006 | Felix | 606/61 |
| 2006/0149244 A1 * 7/2006 | Amrein et al. | 606/61 |
| 2006/0155278 A1 7/2006 | Warnick | |
| 2006/0173454 A1 8/2006 | Spitler et al. | |
| 2006/0200128 A1 9/2006 | Mueller | |
| 2006/0200149 A1 * 9/2006 | Hoy et al. | 606/72 |
| 2006/0229615 A1 10/2006 | Abdou | 606/61 |
| 2006/0235393 A1 10/2006 | Bono et al. | 606/61 |
| 2007/0043355 A1 * 2/2007 | Bette et al. | 606/61 |
| 2007/0043357 A1 2/2007 | Kirschman | |
| 2007/0055235 A1 3/2007 | Janowski et al. | |
| 2007/0055242 A1 3/2007 | Bailly | |
| 2007/0093817 A1 4/2007 | Barrus et al. | |
| 2007/0093827 A1 * 4/2007 | Warnick | 606/61 |
| 2007/0093831 A1 * 4/2007 | Abdelgany et al. | 606/61 |
| 2007/0093833 A1 4/2007 | Kuiper et al. | |
| 2007/0100341 A1 * 5/2007 | Reglos et al. | 606/61 |
| 2007/0123860 A1 * 5/2007 | Francis et al. | 606/61 |
| 2007/0123862 A1 5/2007 | Warnick | |
| 2007/0123865 A1 * 5/2007 | Schlapfer et al. | 606/61 |
| 2007/0123867 A1 5/2007 | Kirschman | |
| 2007/0162008 A1 * 7/2007 | Cline et al. | 606/61 |
| 2007/0225707 A1 * 9/2007 | Wisnewski et al. | 606/61 |
| 2007/0225708 A1 * 9/2007 | Biedermann et al. | 606/61 |
| 2007/0225711 A1 9/2007 | Ensign | |
| 2007/0233080 A1 10/2007 | Na et al. | |
| 2007/0233087 A1 * 10/2007 | Schlapfer | 606/61 |
| 2007/0260246 A1 * 11/2007 | Biedermann | 606/61 |
| 2008/0004627 A1 1/2008 | Dalton | |
| 2008/0015579 A1 * 1/2008 | Whipple | 606/61 |
| 2008/0027432 A1 * 1/2008 | Strauss et al. | 606/61 |
| 2008/1002743 1/2008 | Strauss et al. | |
| 2008/0045951 A1 2/2008 | Fanger et al. | |
| 2008/0045956 A1 2/2008 | Songer et al. | |
| 2008/0058809 A1 3/2008 | Graf | |
| 2008/0058812 A1 3/2008 | Zehnder | |
| 2008/0071277 A1 * 3/2008 | Warnick | 606/73 |
| 2008/0082171 A1 4/2008 | Kuiper et al. | |
| 2008/0091200 A1 4/2008 | Kuiper et al. | |
| 2008/0091204 A1 4/2008 | Kuiper et al. | |
| 2008/0091205 A1 4/2008 | Kuiper et al. | |
| 2008/0154308 A1 * 6/2008 | Sherman et al. | 606/265 |
| 2008/0161859 A1 * 7/2008 | Nilsson | 606/266 |
| 2008/0161863 A1 * 7/2008 | Arnold et al. | 606/319 |
| 2008/0183214 A1 * 7/2008 | Copp et al. | 606/265 |
| 2008/0183216 A1 * 7/2008 | Jackson | 606/278 |
| 2008/0195156 A1 * 8/2008 | Ainsworth et al. | 606/279 |
| 2008/0234734 A1 * 9/2008 | Walder et al. | 606/246 |
| 2008/0234757 A1 * 9/2008 | Jacofsky et al. | 606/308 |
| 2008/0249570 A1 * 10/2008 | Carson et al. | 606/264 |
| 2009/0005817 A1 * 1/2009 | Friedrich et al. | 606/246 |
| 2009/0012567 A1 * 1/2009 | Biedermann et al. | 606/246 |
| 2009/0069849 A1 * 3/2009 | Oh et al. | 606/246 |
| 2009/0118767 A1 * 5/2009 | Hestad et al. | 606/279 |
| 2010/0010544 A1 * 1/2010 | Fallin et al. | 606/264 |
| 2010/0094344 A1 * 4/2010 | Trieu | 606/246 |
| 2010/0094349 A1 * 4/2010 | Hammer et al. | 606/264 |
| 2010/0114168 A1 * 5/2010 | Miller | 606/264 |
| 2010/0114170 A1 * 5/2010 | Barrus et al. | 606/264 |
| 2010/0174313 A1 * 7/2010 | Abdelgany et al. | 606/246 |
| 2010/0234891 A1 * 9/2010 | Freeman et al. | 606/266 |
| 2010/0249845 A1 * 9/2010 | Meunier et al. | 606/263 |
| 2010/0298884 A1 * 11/2010 | Faizan et al. | 606/266 |
| 2010/0312279 A1 * 12/2010 | Gephart et al. | 606/264 |
| 2010/0312282 A1 * 12/2010 | Abdou | 606/279 |
| 2010/0331886 A1 * 12/2010 | Fanger et al. | 606/264 |
| 2010/0331887 A1 * 12/2010 | Jackson et al. | 606/264 |
| 2011/0004245 A1 * 1/2011 | Wu et al. | 606/246 |
| 2011/0077689 A1 * 3/2011 | Mickiewicz et al. | 606/277 |

OTHER PUBLICATIONS

Spinal Concepts, Inc., "The Bac-Fix: Posterior Lower Back Fixation System Surgical Technique," Aug. 1997, 13 pages.
http://www.newsrx.com/newsletter/Medical-Devices-and-Surgical-Technology-Week/2002-09-29/20020929333331QW.html, 1 page.

Office Action issued in U.S. Appl. No. 12/174,438, mailed Jul. 25, 2011, 7 pages.
Office Action issued in U.S. Appl. No. 12/165,724, mailed Jul. 25, 2011, 7 pages.

* cited by examiner

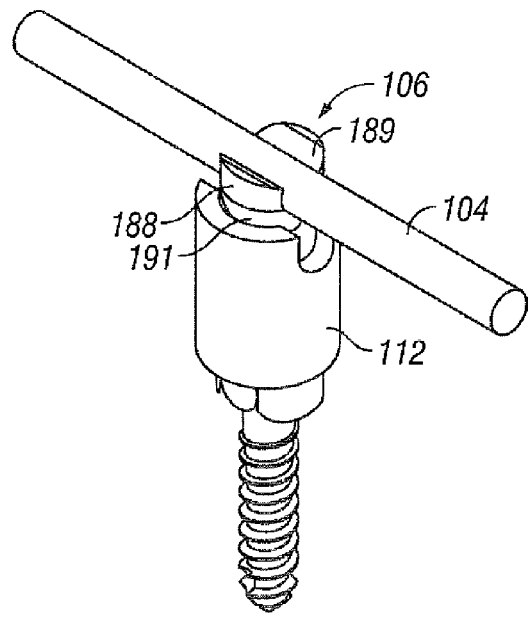
FIG. 5A
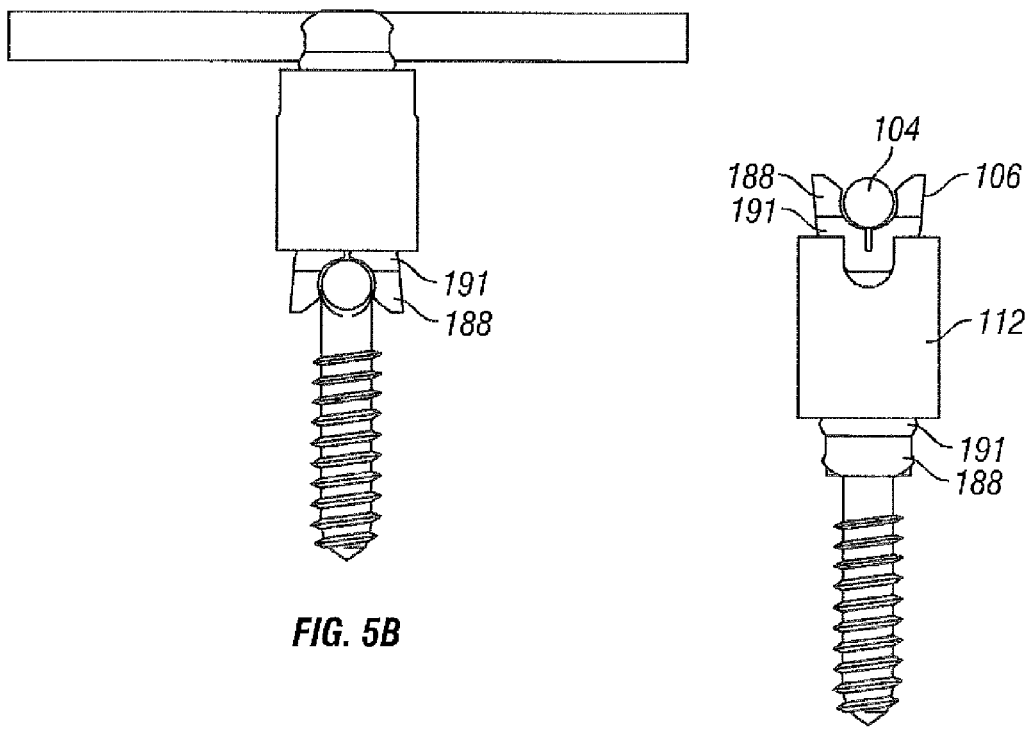
FIG. 5B
FIG. 5C

SYSTEM AND METHOD FOR SPINE STABILIZATION USING RESILIENT INSERTS

BACKGROUND

1. Field of the Disclosure

The present disclosure generally relates to spinal stabilization systems. More particularly, embodiments of the disclosure relate to spinal stabilization systems that may have non-threaded portions for securing rods to bone fasteners.

2. Description of Related Art

Bone may be subject to degeneration caused by trauma, disease, and/or aging. Degeneration may destabilize bone and affect surrounding structures. For example, destabilization of a spine may result in alteration of a natural spacing between adjacent vertebrae. Alteration of a natural spacing between adjacent vertebrae may subject nerves that pass between vertebral bodies to pressure. Pressure applied to the nerves may cause pain and/or nerve damage. Maintaining the natural spacing between vertebrae may reduce pressure applied to nerves that pass between vertebral bodies. A spinal stabilization procedure may be used to maintain the natural spacing between vertebrae and promote spinal stability.

Spinal stabilization may involve accessing a portion of the spine through soft tissue. Spinal stabilization systems for a lumbar region of the spine may be inserted during a spinal stabilization procedure using a posterior spinal approach. Minimally invasive procedures and systems may reduce recovery time as well as trauma to the soft tissue surrounding a stabilization site.

SUMMARY

A spinal stabilization system may be installed in a patient to stabilize a portion of a spine. A spinal stabilization system may be installed using a minimally invasive procedure. An instrumentation kit may provide instruments and spinal stabilization system components necessary for forming a spinal stabilization system in a patient.

A spinal stabilization system may be used to achieve rigid pedicle fixation while minimizing the amount of damage to surrounding tissue. In some embodiments, a spinal stabilization system may be used to provide stability to two or more vertebrae. A spinal stabilization system may include a rod, two or more bone fastener assemblies, and/or a resilient insert. The bone fastener assembly may include a bone fastener and a cylindrical body. A first portion of the bone fastener may couple to a portion of the spine during use. A first portion of a cylindrical body may couple to a second portion of the bone fastener. A second portion of the cylindrical body may couple to a rod during use. In some embodiments, an orientation of the bone fastener may be independent of the orientation of the cylindrical body for a bone fastener assembly. After the bone fastener is placed in a vertebral body, the cylindrical body coupled to the bone fastener may be positioned so that the rod can be positioned in the cylindrical body and in at least one other cylindrical body that is coupled to another vertebral body by a bone fastener.

Embodiments disclosed herein may be directed to an apparatus for anchoring a rod to a bone fastener. The apparatus may include a first resilient insert having a first set of two deflectable arms and a first channel formed between the first set of two deflectable arms, a second resilient insert having a second set of two deflectable arms and a second channel formed between the second set of two deflectable arms, and a cylindrical body having a passage from a first end to a second end therein, wherein the passage in the cylindrical body has an inner diameter. In some embodiments, the first resilient insert has a width greater than the inner diameter of the cylindrical body when the first resilient insert is in a neutral state. In some embodiments, advancement of the first resilient insert into the passage in the cylindrical body deflects the first set of two deflectable arms inward, causing the width of the first channel to decrease, and inhibiting the first resilient insert from moving relative to the cylindrical body. In some embodiments, the second resilient insert has a width greater than the inner diameter of the cylindrical body when the second resilient insert is in a neutral state. In some embodiments, advancement of the second resilient insert into the passage in the cylindrical body deflects the second set of two deflectable arms inward, causing the width of the second channel to decrease and inhibiting the second resilient insert from moving relative to the cylindrical body. In some embodiments, at least one of the first set of two deflectable arms and the second set of the two deflectable arms comprise beveled surfaces proximate the first channel or the second channel. In some embodiments, at least one of the first set of two deflectable arms and the second set of the two deflectable arms comprise radiused surfaces proximate the first channel or the second channel. In some embodiments, the second end of the cylindrical body comprises two recessed portions, wherein each recessed portion has an associated width greater than the diameter of the rod. In some embodiments, the first channel in the first resilient insert comprises a first slot. In some embodiments, compression of the first slot deflects the first set of two deflectable arms inward to decrease the width of the first channel. In some embodiments, the second channel in the second resilient insert comprises a second slot. In some embodiments, compression of the second slot deflects the second set of two deflectable arms inward to decrease the width of the second channel. In some embodiments, at least one of the first resilient insert and the second resilient insert is cannulated.

Embodiments disclosed herein may be directed to a system for stabilizing a portion of a spine. The system may include a rod having a substantially circular cross-sectional geometry, two or more bone fasteners, two or more anchor assemblies, and a cylindrical body having a passage from a first end to a second end, wherein the passage in the cylindrical body has an inner diameter. In some embodiments, each bone fastener comprises a threaded shank and a head connected to the threaded shank and having an associated diameter. In some embodiments, each anchor assembly comprises a first resilient insert having a first set of two deflectable arms and a first channel formed between the first set of two deflectable arms, a second resilient insert having a second set of two deflectable arms and a second channel formed between the second set of two deflectable arms, and a cylindrical body having a passage from a first end to a second end. In some embodiments, the first resilient insert has a width greater than the inner diameter of the cylindrical body when the first resilient insert is in a neutral state. In some embodiments, advancement of the first resilient insert into the passage in the cylindrical body deflects the first set of two deflectable arms inward, causing the width of the first channel to decrease, and inhibiting the first resilient insert from moving relative to the cylindrical body. In some embodiments, the second resilient insert has a width greater than the inner diameter of the cylindrical body when the second resilient insert is in a neutral state. In some embodiments, advancement of the second resilient insert into the passage in the cylindrical body deflects the second set of two deflectable arms inward, causing the width of the second channel to decrease and inhibiting the second resilient insert from moving relative to the cylindrical body. In some embodiments, at least one of the first set of two deflectable arms and the second set of the two deflectable arms comprise beveled surfaces proximate the first channel or the second channel. In some embodiments, at least one of the first set of two deflectable arms and the second set of the two deflectable arms comprise radiused surfaces proximate the first channel or the second channel. In some embodiments, the second end of the cylindrical body comprises two recessed portions, wherein each recessed portion has an associated width greater than the diameter of the rod. In some embodiments, the first channel in the first resilient insert comprises a first slot, wherein compression of the first slot deflects the first set of two deflectable arms inward to decrease the width of the first channel. In some embodiments, compression of the second slot deflects the second set of two deflectable arms inward to decrease the width of the second channel.

Embodiments disclosed herein may be directed to a method for coupling a rod to a portion of the spine. The method may include advancing a bone fastener into a vertebral body, advancing a first resilient insert onto the head of the bone fastener, positioning a passage of a first end of a cylindrical body over the first resilient insert, positioning a second resilient insert in the second end of the cylindrical body, positioning a portion of a rod in the second channel in the second resilient insert, and advancing the first resilient insert and the second resilient insert into the cylindrical body. In some embodiments, the bone fastener comprises a head having an associated diameter and a threaded shank connected to the head. In some embodiments, the first resilient insert comprises a first set of two deflectable arms and a first channel formed between the first set of two deflectable arms, wherein the width of the first channel of the first resilient insert is greater than the diameter of the head of the bone fastener when the first resilient insert is in a neutral state. In some embodiments, the second resilient insert comprises a second set of two deflectable arms and a second channel formed between the second set of two deflectable arms, wherein the width of the second channel of the second resilient insert is greater than the diameter of a rod when the second resilient insert is in a neutral state. In some embodiments, a width of the first resilient insert is greater than the inner diameter of the passage of the cylindrical body. In some embodiments, advancing the first resilient insert into the passage in the cylindrical body deflects the first set of two deflectable arms inward, causing the width of the first channel to decrease and inhibiting the bone fastener positioned in the first channel of the first resilient insert from moving relative to the first resilient insert. In some embodiments, a width of the second resilient insert is greater than the inner diameter of the passage of the cylindrical body. In some embodiments, advancing the second resilient insert into the passage in the cylindrical body deflects the second set of two deflectable arms inward, causing the width of the second channel to decrease and inhibiting the rod positioned in the second channel of the second resilient insert from moving relative to the second resilient insert.

In some embodiments, at least one of the first set of two deflectable arms and the second set of the two deflectable arms comprise beveled surfaces proximate the first channel or the second channel. In some embodiments, at least one of the first set of two deflectable arms and the second set of the two deflectable arms comprise radiused surfaces proximate the first channel or the second channel. In some embodiments, the second end of the cylindrical body comprises two recessed portions, wherein each recessed portion has an associated width greater than the diameter of the rod. In some embodiments, at least one of the first set of two deflectable arms and the second set of two deflectable arms has a first width and a second width that is greater than the first width. In some embodiments, advancing the first resilient insert into the cylindrical body comprises advancing the first resilient insert until the first width thereof contacts interior walls of the second end of the cylindrical body and the second width thereof is compressed against the interior walls of the second end of the cylindrical body. In some embodiments, advancing the second resilient insert into the cylindrical body comprises advancing the second resilient insert until the first width thereof contacts interior walls of the second end of the cylindrical body and the second width thereof is compressed against the interior walls of the second end of the cylindrical body. In some embodiments, the channel in each resilient insert comprises a slot such that compression of the slot deflects the two deflectable arms inward. In some embodiments, one or more steps are performed using Minimally Invasive Surgery (MIS) procedures. In some embodiments, at least one of the two resilient inserts is cannulated.

Different instruments may be used to form a spinal stabilization system in a patient using a minimally invasive procedure. The instruments may include, but are not limited to, positioning needles, guide wires, sleeves, bone fastener driver, mallets, tissue wedges, tissue retractors, tissue dilators, bone awls, taps, and a rod length estimator. An instrumentation kit may include, but is not limited to, two or more detachable members (e.g., sleeves), a tissue wedge, a rod positioner, a counter torque wrench, an estimating tool, a seater, insert driver, and/or combinations thereof.

Other objects and advantages of the embodiments disclosed herein will be better appreciated and understood when considered in conjunction with the following description and the accompanying drawings.

BRIEF DESCRIPTION OF THE DRAWINGS

Advantages of the present disclosure will become apparent to those skilled in the art with the benefit of the following detailed description and upon reference to the accompanying drawings in which:

FIGS. 5A-5C depict perspective, side and end views of a portion of one embodiment of a spine stabilization system;

Figure 1:
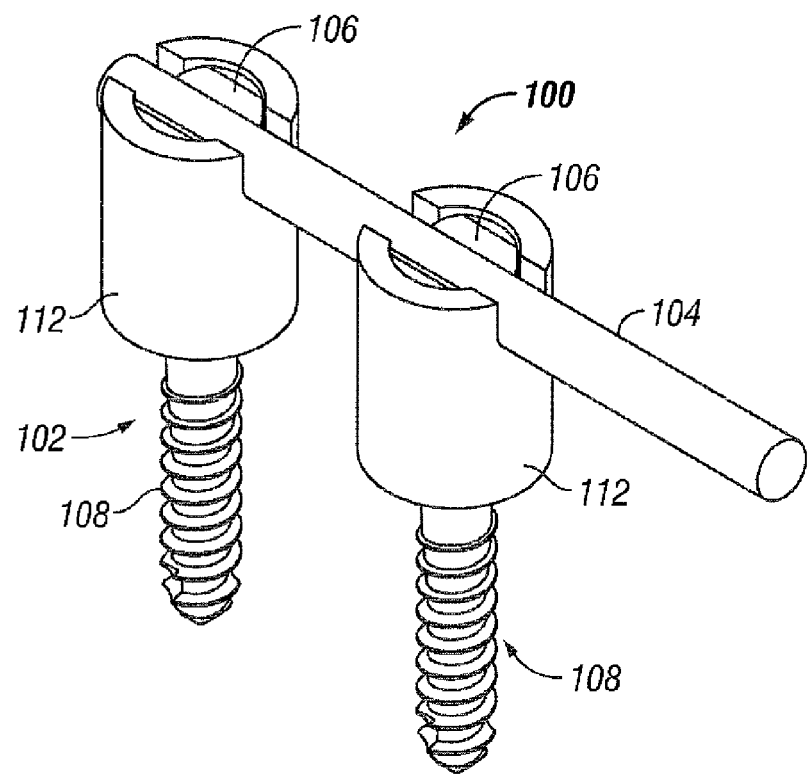
FIG. 1 depicts a perspective view of one embodiment of a spinal stabilization system.

While the disclosure is susceptible to various modifications and alternative forms, specific embodiments thereof are shown by way of example in the drawings and will herein be described in detail. The drawings may not be to scale. It should be understood that the drawings and detailed description thereto are not intended to limit the disclosure to the particular form disclosed, but on the contrary, the intention is to cover all modifications, equivalents, and alternatives falling within the spirit and scope of the present disclosure as defined by the appended claims.

DETAILED DESCRIPTION

The invention and the various features and advantageous details thereof are explained more fully with reference to the non-limiting embodiments that are illustrated in the accompanying drawings and detailed in the following description. Descriptions of well known starting materials, processing techniques, components and equipment are omitted so as not to unnecessarily obscure the disclosure in detail. Skilled artisans should understand, however, that the detailed description and the specific examples, while disclosing preferred embodiments, are given by way of illustration only and not by way of limitation. Various substitutions, modifications, additions or rearrangements within the scope of the underlying inventive concept(s) will become apparent to those skilled in the art after reading this disclosure.

As used herein, the terms "comprises," "comprising," "includes," "including," "has," "having" or any other variation thereof, are intended to cover a non-exclusive inclusion. For example, a process, product, article, or apparatus that comprises a list of elements is not necessarily limited to only those elements but may include other elements not expressly listed or inherent to such process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of, any term or terms with which they are utilized. Instead these examples or illustrations are to be regarded as being described with respect to one particular embodiment and as illustrative only. Those of ordinary skill in the art will appreciate that any term or terms with which these examples or illustrations are utilized encompass other embodiments as well as implementations and adaptations thereof which may or may not be given therewith or elsewhere in the specification and all such embodiments are intended to be included within the scope of that term or terms. Language designating such non-limiting examples and illustrations includes, but is not limited to: "for example," "for instance," "e.g.," "in one embodiment," and the like.

A spinal stabilization system may be installed in a patient to stabilize a portion of a spine. Spinal stabilization may be used, but is not limited to use, in patients having degenerative disc disease, spinal stenosis, spondylolisthesis, pseudoarthrosis, and/or spinal deformities; in patients having fracture or other vertebral trauma; and in patients after tumor resection. A spinal stabilization system may be installed using a minimally invasive procedure. An instrumentation set may include instruments and spinal stabilization system components for forming a spinal stabilization system in a patient.

A minimally invasive procedure may be used to limit an amount of trauma to soft tissue surrounding vertebrae that are to be stabilized. In some embodiments, the natural flexibility of skin and soft tissue may be used to limit the length and/or depth of an incision or incisions needed during the stabilization procedure. Minimally invasive procedures may provide limited direct visibility in vivo. Forming a spinal stabilization system using a minimally invasive procedure may include using tools to position system components in the body.

A minimally invasive procedure may be performed after installation of one or more spinal implants in a patient. The spinal implant or spinal implants may be inserted using an anterior procedure and/or a lateral procedure. The patient may be turned and a minimally invasive procedure may be used to install a posterior spinal stabilization system. A minimally invasive procedure for stabilizing the spine may be performed without prior insertion of one or more spinal implants in some patients. In some patients, a minimally invasive procedure may be used to install a spinal stabilization system after one or more spinal implants are inserted using a posterior spinal approach.

A spinal stabilization system may be used to achieve rigid fixation while minimizing the amount of damage to surrounding tissue. In some embodiments, a spinal stabilization system may be used to provide stability to two adjacent vertebrae (i.e., one vertebral level). A spinal stabilization system may include two bone fastener assemblies. One bone fastener assembly may be positioned in each of the vertebrae to be stabilized. A rod may be coupled and secured to the bone fastener assemblies. As used herein, "coupled" components may directly contact each other or may be separated by one or more intervening members. In some embodiments, a single spinal stabilization system may be installed in a patient. Such a system may be referred to as a unilateral, single-level stabilization system or a single-level, two-point stabilization system. In some embodiments, two spinal stabilization systems may be installed in a patient on opposite sides of a spine. Such a system may be referred to as a bilateral, single-level stabilization system or a single-level, four-point stabilization system.

In some embodiments, a spinal stabilization system may provide stability to three or more vertebrae (i.e., two or more vertebral levels). In a two vertebral level spinal stabilization system, the spinal stabilization system may include three bone fastener assemblies. One bone fastener assembly may be positioned in each of the vertebrae to be stabilized. A rod may be coupled and secured to the three bone fastener assemblies. In some embodiments, a single two-level spinal stabilization system may be installed in a patient. Such a system may be referred to as a unilateral, two-level stabilization system or a two-level, three-point stabilization system. In some embodiments, two three-point spinal stabilization systems may be installed in a patient on opposite sides of a spine. Such a system may be referred to as a bilateral, two-level stabilization system or a two-level, six-point stabilization system.

In some embodiments, combination systems may be installed. For example, a two-point stabilization system may be installed on one side of a spine, and a three-point stabilization system may be installed on the opposite side of the spine. The composite system may be referred to a five-point stabilization system.

Minimally invasive procedures may reduce trauma to soft tissue surrounding vertebrae that are to be stabilized. Only a small opening may need to be made in a patient. For example, for a single-level stabilization procedure on one side of the spine, the surgical procedure may be performed through a 2 cm to 4 cm incision formed in the skin of the patient. In some embodiments, the incision may be above and substantially between the vertebrae to be stabilized. In some embodiments, the incision may be above and between the vertebrae to be stabilized. In some embodiments, the incision may be above and substantially halfway between the vertebrae to be stabilized. Dilators, a targeting needle, and/or a tissue wedge may be used to provide access to the vertebrae to be stabilized without the need to form an incision with a scalpel through muscle and other tissue between the vertebrae to be stabilized. A minimally invasive procedure may reduce an amount of post-operative pain felt by a patient as compared to invasive spinal stabilization procedures. A minimally invasive procedure may reduce recovery time for the patient as compared to invasive spinal procedures.

Components of spinal stabilization systems may be made of materials including, but not limited to, titanium, titanium alloys, stainless steel, ceramics, and/or polymers. Some components of a spinal stabilization system may be autoclaved and/or chemically sterilized. Components that may not be autoclaved and/or chemically sterilized may be made of sterile materials. Components made of sterile materials may be placed in working relation to other sterile components during assembly of a spinal stabilization system. Likewise, instruments used to install a spinal stabilization system may be made of materials including, but not limited to, stainless steel, titanium, titanium alloys, ceramics, and/or polymers. Some instruments may be autoclaved and/or chemically sterilized. Some instruments may include components that cannot be autoclaved or chemically sterilized. Components of instruments that cannot be autoclaved or chemically sterilized may be made of sterile materials. The sterile materials may be placed in working relation to other parts of the instrument that have been sterilized.

Spinal stabilization systems may be used to correct problems in lumbar, thoracic, and/or cervical portions of a spine. Various embodiments of a spinal stabilization system may be used from the C1 vertebra to the sacrum. For example, a spinal stabilization system may be implanted posterior to the spine to maintain distraction between adjacent vertebral bodies in a lumbar portion of the spine.

Reference is now made in detail to the exemplary embodiments, examples of which are illustrated in the accompanying drawings. Wherever possible, the same reference numbers will be used throughout the drawings to refer to the same or like parts (elements).

FIG. 1 depicts one embodiment of spinal stabilization system 100 that may be implanted using a minimally invasive surgical procedure. Spinal stabilization system 100 may include rod 104 and bone fastener assemblies 102 including bone fasteners 108, cylindrical bodies 112 and resilient inserts 106. Other spinal stabilization system embodiments may include, but are not limited to, plates, dumbbell-shaped members, and/or transverse connectors. FIG. 1 depicts a spinal stabilization system for one vertebral level. In some embodiments, the spinal stabilization system of FIG. 1 may be used as a multi-level spinal stabilization system if one or more vertebrae are located between the vertebrae in which bone fastener assemblies 102 are placed. In some embodiments, multi-level spinal stabilization systems may include additional bone fastener assemblies 102 to couple to one or more other vertebrae.

Figure 2A:
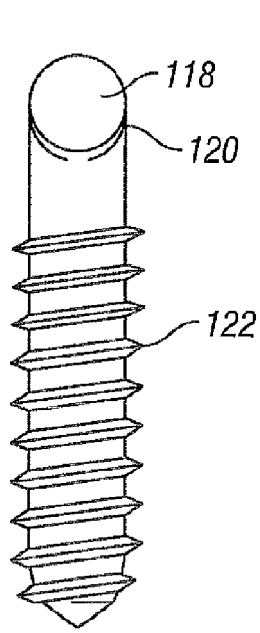
FIGS. 2A-2C depict side and perspective views of one embodiment of a bone fastener.
Figure 2B:
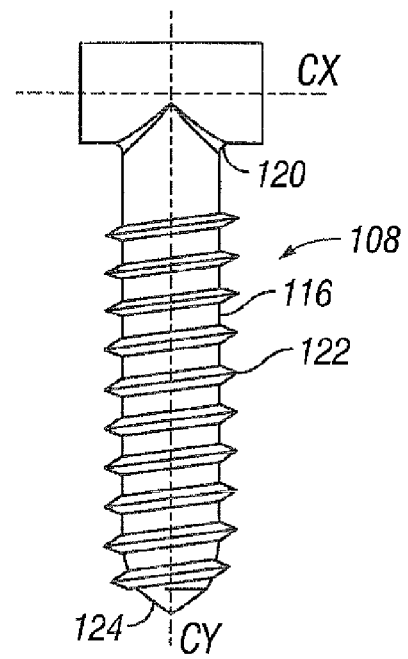
Figure 2C:
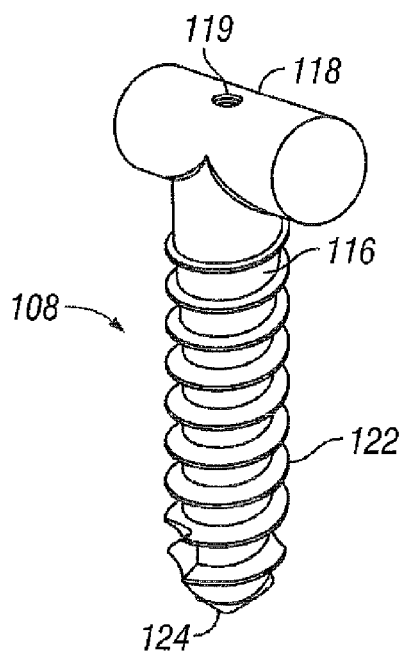

FIGS. 2A-2C depict side and perspective views of one embodiment of bone fastener 108. In some embodiments, head 118 of bone fastener 108 may include various configurations or geometries to couple with resilient insert 106. In some embodiments, head 118 may have a substantially circular cross-sectional geometry as shown in FIG. 2A. Threads 122 may be used to engage vertebral bone to implant bone fastener 108. In some embodiments, head 118 may be shaped with a cylindrical profile having a central axis CX oriented perpendicular to the longitudinal axis CY of shank 116, such as depicted in FIG. 2B. Head 118 may have a cylindrical appearance as depicted in FIG. 2C. In some embodiments, head 118 may have a substantially spherical geometry. Surface of head 118 of bone fastener 108 may be machined for selected contact with resilient insert 106. Head 118 may be grooved, knurled, bead blasted, or otherwise machined for increased friction between head 118 and resilient insert 106. In some embodiments, head 118 may include various configurations for engagement by a driver or other tool. In some embodiments, a driver may also be used to remove an installed bone fastener 108 from a vertebra.

FIG. 2C depicts a perspective view of bone fastener 108. Bone fastener 108 may include shank 116 and head 118. Shank 116 may include threading 122. In some embodiments, threading 122 may include self-tapping start 124. Self-tapping start 124 may facilitate insertion of bone fastener 108 into vertebral bone. Bone fasteners 108 may be provided in various lengths in an instrumentation set to accommodate variability in vertebral bodies. For example, an instrumentation set for stabilizing vertebrae in a lumbar region of the spine may include bone fasteners 108 with lengths ranging from about 30 mm to about 75 mm in 5 mm increments. A bone fastener 108 may be stamped with indicia (i.e., printing on the head). In some embodiments, bone fastener 108 may be color-coded to indicate a length of bone fastener 108. In some embodiments, bone fastener 108 with a 30 mm thread length may have a magenta color, bone fastener 108 with a 35 mm thread length may have an orange color, and bone fastener 108 with a 55 mm thread length may have a blue color. Other colors may be used as desired.

Each bone fastener 108 provided in an instrumentation set may have substantially the same thread profile and thread pitch. In one embodiment, the thread may have about a 4 mm major diameter and about a 2.5 mm minor diameter with a cancellous thread profile. In some embodiments, the minor diameter of the thread may be in a range from about 1.5 mm to about 4 mm or larger. In some embodiments, the major diameter of the thread may be in a range from about 3.5 mm to about 6.5 mm or larger. Bone fasteners 108 with other thread dimensions and/or thread profiles may also be used. A thread profile of bone fasteners 108 may allow bone purchase to be maximized when bone fastener 108 is positioned in vertebral bone.

In some embodiments, bone fastener 108 may include neck 120. In some embodiments, neck 120 may be sized and shaped for movement of cylindrical body 112 relative to bone fastener 108. In some embodiments, an instrumentation set may contain bone fasteners 108 with necks 120 of various shapes, sizes, and dimensions for use in spine stabilization systems 100. In some embodiments, neck 120 of bone fastener 108 may have a smaller diameter than adjacent portions of head 118 and shank 116. The diameter of neck 120 may fix the maximum angle that cylindrical body 112 can rotate relative to bone fastener 108. In some embodiments, neck 120 may be sized to allow up to about 40 degrees or more of angulation of cylindrical body 112 relative to bone fastener 108. In some embodiments, neck 120 may be sized to allow up to about 30 degrees or more of angulation of cylindrical body 112 relative to bone fastener 108. In some embodiments, neck 120 may be sized to allow up to about 20 degrees or more of angulation of cylindrical body 112 relative to bone fastener 108. In some embodiments, bone fastener 108 may be cannulated for use in a minimally invasive procedure. In some embodiments, cannulated passage 119 may run along longitudinal axis CY of bone fastener 108. In some embodiments, neck 120 may have a recessed portion for rotation inside resilient insert 106. In some embodiments, the recessed portion may have a unique radius.

Figure 3A:
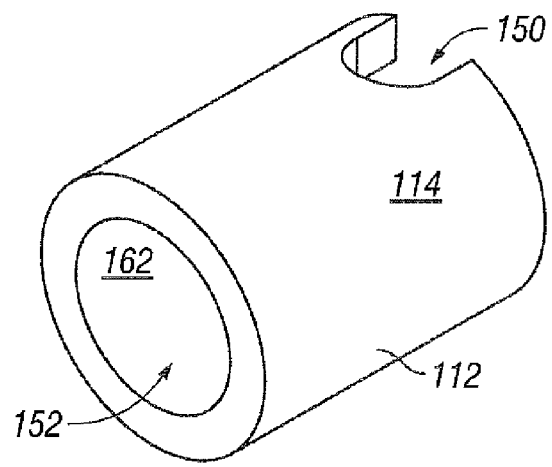
FIGS. 3A and 3B depict perspective and side views of one embodiment of a cylindrical body.
Figure 3B:
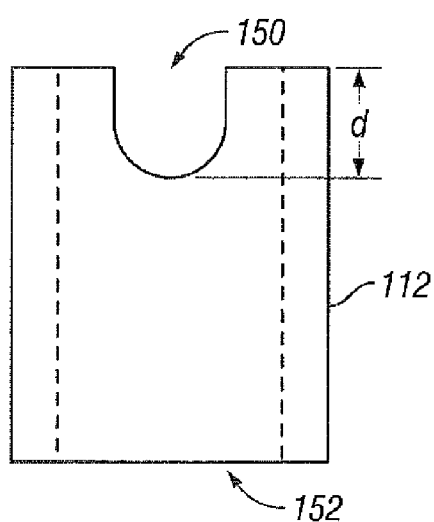

In some embodiments, a cylindrical body may be used to couple a rod to a bone fastener engaged in a vertebral body. FIGS. 3A and 3B depict perspective and side views of one embodiment of cylindrical body 112. Cylindrical body 112 may receive elements including, but not limited to, bone fastener 108, resilient insert 106, and rod 104. In some embodiments, cylindrical body 112 may couple two or more other elements together (e.g., rod 104 and bone fastener 108). Cylindrical body 112 may have any of various physical forms. In some embodiments, rod 104 may be top loaded into resilient insert 106. Resilient insert 106 may be inserted in cylindrical body 112 to couple rod 104 to cylindrical body 112.

Cylindrical body 112 may include central passage 152. Central passage 152 may be formed in cylindrical body 112 from a first end to a second end. Inner surface 162 of central passage 152 may be machined to complement a portion of an outer surface of resilient insert 106 that is to be positioned in cylindrical body 112. Machining of inner surface 162 may enhance retention of resilient insert 106 in cylindrical body 112. Central passage 152 of cylindrical body 112 may be complementary in shape to a portion resilient insert 106 so that resilient insert 106 is able to swivel in cylindrical body 112. Inner surfaces and/or outer surfaces of cylindrical body 112 may be surface treated or include coatings and/or coverings to modify frictional properties or other properties of cylindrical body 112.

In some embodiments, cylindrical body 112 may include recessed portions 150. Recessed portions 150 may accommodate rod 104. In some embodiments, the depth d of recessed portions 150 may be shallow (i.e., less than the diameter of rod 104). In some embodiments, the depth d of recessed portions 150 may be deep (i.e., greater than the diameter of rod 104). Recessed portions 150 may include, but are not limited to, an elongated opening of constant width, an elongated opening of variable width, an angular opening, a curved opening, a tapered opening, and combinations and/or portions thereof. In some embodiments, a first portion of recessed portions 150 may have different dimensions than a second portion of recessed portions 150. In some embodiments, a portion of recessed portions 150 on a first side of cylindrical body 112 may have different dimensions than a portion of recessed portions 150 on a second side of cylindrical body 112.

Figure 4A:
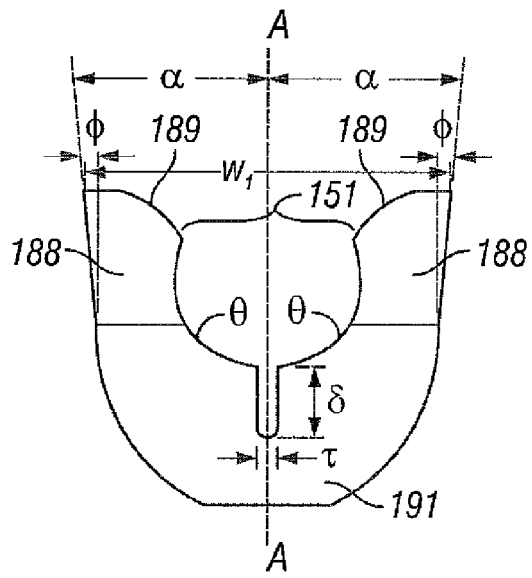
FIGS. 4A-4C depict end and top views of one embodiment of a resilient insert.
Figure 4C:
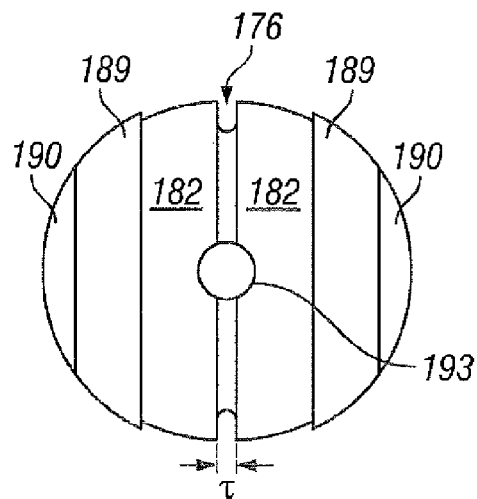
Figure 4B:
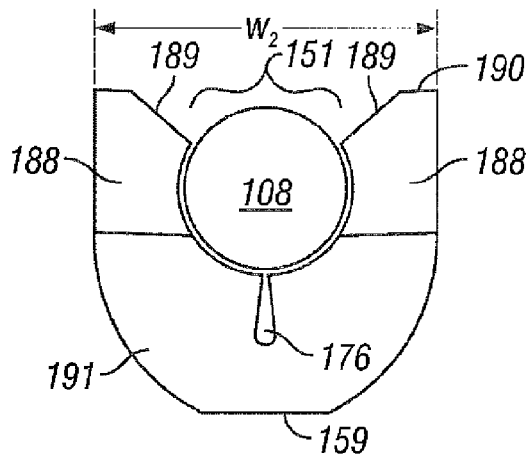

In some embodiments, resilient inserts may be advanced into cylindrical bodies to securely couple a rod to the cylindrical body or to securely couple a bone fastener to the cylindrical body. FIGS. 4A-4C depict end and top views of one embodiment of resilient insert 106. Resilient inserts 106 may be coupled to cylindrical bodies 112 of bone fastener assemblies 102 to couple rod 104 to cylindrical body 112 or to couple cylindrical body 112 to bone fastener 108. In some embodiments, resilient insert 106 may be cannulated.

FIGS. 4A-4C depict resilient insert 106 prior to insertion of resilient insert 106 into cylindrical body 112 of bone fastener assembly 102. In some embodiments, resilient insert 106 may include channel 151 for coupling to bone fastener 108. Channel 151 may have an associated diameter or radius of curvature. In some embodiments, channel 151 may have a first diameter when resilient insert 106 is in a neutral state (i.e., has width $w_1$) and a second diameter when resilient insert 106 is compressed (i.e., has width $w_2$). In some embodiments, changing the diameter or radius of curvature changes the friction force exerted on rod 104 positioned in channel 151. Changing the friction force can change the rigidity of spine stabilization system 100.

As shown in FIG. 4A, resilient insert 106 may be have an associated taper α (Alpha). In some embodiments, a tapered portion of resilient insert 106 may be the result of a second portion of resilient insert 106 formed into a frustum. In some embodiments, decreasing the taper α (Alpha) of resilient insert 106 decreases the width of channel 151. If rod 104 is positioned in channel 151, rod 104 may be captured or otherwise securely coupled to resilient insert 106 when taper α (Alpha) decreases. In some embodiments, rod 104 may be captured by resilient insert 106 when taper α (Alpha) is 0 degrees. In some embodiments, rod 104 may be captured by resilient insert 106 when taper α (Alpha) is less than 5 degrees. In some embodiments, rod 104 may be captured by resilient insert 106 when taper α (Alpha) is less than 10 degrees.

Resilient inert 106 may include a set of two deflectable arms 188 formed by channel 151. In some embodiments, the taper α (Alpha) of resilient insert 106 may be due to deflectable arms 188. In some embodiments, the taper α (Alpha) associated with resilient insert 106 may be due to an increase in the thickness of the distal ends of deflectable arms 188. In some embodiments, the taper α (Alpha) associated with resilient insert 106 may be due to the geometry of deflectable arms 188. Deflectable arms 188 may extend at some angle γ (phi) relative to the longitudinal axis AA of resilient insert 106. In some embodiments, deflection of arms 188 inward (i.e., angle φ (phi) of deflectable arms 188 decreases) decreases the taper α (Alpha) of resilient insert 106, which decreases the changes the width of channel 151 from $w_1$ to $w_2$.

In FIGS. 4A and 4C, resilient insert 106 is shown in a first state (i.e., resilient insert 106 is in a neutral state) having an associated taper α (Alpha), and slot 176 in portion 191 of resilient insert 106 has an associated width T (tau). In some embodiment, closing or partially closing slot 176 located in a first portion 192 of resilient insert 106 may decrease the taper α (Alpha) of resilient insert 106. As used herein, the term "closing" generally refers to decreasing the opening of slot 176 using compression, torsion, or some combination to decrease the distance between arms 188. Thus, closing slot 176 may result in the sides of slot 176 touching or not touching at any point in slot 176. In FIG. 4B, resilient insert 106 is shown in a second state (i.e., resilient insert 106 is compressed) having substantially 0 degrees of taper, and slot 176 is closed or partially closed to decrease the distance between arms 188 to capture rod 104, but deflectable arms 188 have not been deflected. In some embodiments, the change in the taper α (Alpha) and the narrowing of the width of channel 151 of resilient insert 106 may be due solely to the closure or partial closure of slot 176. In some embodiments, the taper α (Alpha) may be changed and the width of channel 151 may be narrowed by a combination of deflecting deflectable arms 188 and closing or partially closing slot 176.

In some embodiments, when resilient insert 106 is compressed, width T (tau) decreases to change the width of channel 151. In some embodiments, when resilient insert 106 is compressed, the radius of curvature (θ) of channel 151 may be decreased to change the width of channel 151. In some embodiments, when resilient insert 106 is compressed, width T (tau) and the radius of curvature (θ) of channel 151 are both decreased to change the width of channel 151.

In some embodiments, channel 151 may have inner surface 182 machined for selected contact with rod 104 or bone fastener 108. Inner surface 182 may be grooved, textured, coated or otherwise machined for coupling resilient insert 106 to rod 104 or head 118 of bone fastener 108. Channel 151 may also include slot 176 having width T (tau) and depth δ (delta).

FIG. 4B depicts an end view of one embodiment of resilient insert 106 coupled to bone fastener 108. Resilient insert 106 may couple to head 118 of bone fastener 108 by decreasing the width of channel 151 to inhibit motion of head 118 of bone fastener 108 relative to resilient insert 106. In some embodiments, resilient insert 106 may include channel 151 for coupling to rod 104, such as shown in FIG. 1. Resilient inert 106 may include a set of two deflectable arms 188 formed by channel 151 in resilient insert 106. Resilient insert 106 may couple to rod 104 by decreasing the width of channel 151 to inhibit motion of rod 104 relative to resilient insert 104. In some embodiments, a first resilient insert 106 may couple cylindrical body 112 to head 118 of bone fastener 108 and a second resilient insert 106 may couple cylindrical body 112 to rod 104. In some embodiments, first resilient insert 106 and 106 are substantially equal.

In some embodiments, resilient insert 106 may have base surface 159. In some embodiments, base surface 159 may be flat or deformable. In some embodiments, base surface 159 on a first resilient insert 106 may contact base surface 159 on a second resilient insert 106 when two resilient inserts 106 are inserted in either end of cylindrical body 112. In some embodiments, base surface 159 of first resilient insert 106 may be deformed when in contact with base surface 159 of second resilient insert 106 or base surface 159 of second resilient insert 106 may be deformed when in contact with base surface 159 of first resilient insert 106.

Still referring to FIGS. 4A-4C, in some embodiments, resilient insert 106 may have radiused or curved surfaces 189. Radiused or curved surfaces 189 may facilitate positioning of rod 104 in resilient insert 106, which may be useful during Minimally Invasive Surgery (MIS). Radiused or curved surfaces 189 may provide more visibility during surgery, which may allow a surgeon to verify the procedure. In some embodiments, when resilient insert 106 is advanced onto head 118 of bone fastener 108, radiused or beveled surfaces 189 may guide resilient insert 106. In MIS procedures, visibility may be limited. Having surfaces 189 to guide resilient insert 106 may reduce the complexity of the surgery, may reduce the number of tools needed during the surgery, may reduce the time spent in surgery, and the like. In some embodiments, resilient insert 106 may have top surface 190. Top surface 190 may be flat, as shown in FIG. 4A, or may be curved. A flat top surface 190 aligned with a surface or feature of cylindrical body 112 may be used to indicate when resilient insert 106 is fully seated in cylindrical body 112.

In some embodiments, resilient insert 106 may be cannulated for use in MIS procedures. FIG. 4C depicts a top view of one embodiment of resilient insert 106 having cannulated passage 193 for use in MIS procedures. Advancing resilient insert 106 to an implantation site using a guide wire or other tool may reduce the size of a wound needed to access the implantation site, may reduce damage to nearby tissue, may reduce soreness or pain in the patient, and other benefits.

A first resilient insert 106 may be rotatably positioned in cylindrical body 112 such that first resilient insert 106 is able to move radially and/or rotationally relative to cylindrical body 112 (or cylindrical body 112 relative to first resilient insert 106) within a defined range of motion. The range of motion may be provided within a plane, such as by first resilient insert 106 rotating about the axis of cylindrical head 118 of bone fastener 108, or within a three-dimensional region, such as by a spherical head 118 (not shown) of bone fastener 108 rotating within first channel in resilient insert 106. A second resilient insert 106 may be rotatably positioned in cylindrical body 112 such that second resilient insert 106 is able to move radially and/or rotationally relative to cylindrical body 112 (or cylindrical body 112 relative to second resilient insert 106) within a defined range of motion. The range of motion may be provided within a plane, such as by second resilient insert 106 rotating about the axis of rod 104, or within a three-dimensional region, such as by resilient insert 106 rotating inside cylindrical body 112. In some embodiments, resilient insert 106 may be able to rotate 360 degrees when positioned in cylindrical body 112.

Bone fastener assemblies 102 may include, but are not limited to, cylindrical bodies 112, resilient inserts 106 and bone fasteners 108. Bone fastener 108 may be advanced into a vertebral body by rotating bone fastener assembly 102 to engage threads 122 of bone fastener 108 with the bony tissue. In some embodiments, the central axis of cylindrical body 112 may be aligned with the longitudinal axis of bone fastener 108. Bone fastener 108 may be angulated in a symmetrical conical range of motion about the aligned axes. Bone fastener 108 may be constrained from motion outside a selected limit axis by contact between neck 120 of bone fastener 108 and cylindrical body 112. Alignment of the central axis of bone fastener 108 with the longitudinal axis of cylindrical body 112 may be considered a neutral position relative to the range of motion. The alignment is a neutral position because bone fastener 108 may be angulated an equal amount in any direction from the central axis of cylindrical body 112. When a driver is inserted into bone fastener 108, the longitudinal axis of bone fastener 108 may be substantially aligned with the central axis of cylindrical body 112 to facilitate insertion of bone fastener 108 into a vertebral body. In some embodiments, the range of motion of cylindrical body 112 about bone fastener 108 may be 360 degrees.

In some embodiments, the angle of the longitudinal axis of a first bone fastener assembly coupled to a first vertebra may differ from the angle of the central axis of a second bone fastener assembly 102 coupled to a second vertebra. By rotating and selectively positioning resilient inserts 106 in cylindrical bodies 112, differences and variations in the angulation of bone fasteners 108 may be accommodated by resilient inserts 106 and cylindrical bodies 112.

Angulation of resilient inserts 106 may allow fine adjustment of engagement angles of bone fasteners 108. In addition, angulation of resilient inserts 106 may allow adjustment in the orientation of bone fasteners 108 in a sagittal plane (i.e., to conform to lordosis of a spine) while still allowing cylindrical bodies 112 to be easily coupled with rod 104. Rod 104 may be disposed in channels 151 and secured by resilient inserts 106. In some embodiments, a flexible driver or a polyaxial driver (e.g., a driver with a universal joint) may be used to drive the heads of bone fasteners 108 from a position that is off-axis from the longitudinal axis of bone fasteners 108 to reduce the size of an opening of the body needed to implant embodiments disclosed herein.

Embodiments disclosed herein include spine stabilization systems that may be assembled without a threaded closure member. By advancing resilient inserts 106 into cylindrical bodies 112, deflectable arms 188 may deflect and/or slots 176 may collapse to capture rod 104 in channel 151.

FIGS. 5A-5C depict perspective, side and front views of one embodiment of a portion of spine stabilization system 100. As shown in FIGS. 5A-5C, resilient inserts 106 may be partially inserted into cylindrical bodies 112, head 118 of bone fastener 108 may be partially inserted into a first resilient insert 106 and rod 104 may be partially positioned in a second resilient insert 106. A first resilient insert 106 need not be aligned with a second resilient insert 106. As shown in FIG. 5A, first resilient insert 106 may be rotated approximately 90 degrees relative to second resilient insert 106. First resilient insert 106 may be seated on head 118 of bone fastener 108. Cylindrical body 112 may be advanced onto first portion 191 of first resilient insert 106 such that cylindrical body 112 may rotate relative to bone fastener 108. In some embodiments, the advancement of cylindrical body 112 onto a first portion of first resilient insert 106 may provisionally couple cylindrical body 112 to first resilient insert 106.

Provisional coupling of cylindrical body 112 to resilient inserts 106 may allow the surgeon to assemble spine stabilization system 100 in steps and to adjust spine stabilization system 100 during surgery. In some embodiments, advancement of cylindrical body 112 onto resilient insert 106 may collapse slot 176 or deflect arms 188 to generate a spring force to provisionally couple cylindrical body 112 to resilient insert 106. In some embodiments, advancement of cylindrical body 112 onto resilient insert 106 may create a friction force to provisionally couple cylindrical body 112 to resilient insert 106.

In some embodiments, cylindrical body 112 may be provisionally coupled to a first resilient insert 106 before coupling to the second resilient insert 106. Thus, in some embodiments, cylindrical body 112 may be provisionally coupled to first resilient insert 106 before second resilient insert 106 is inserted or advanced into cylindrical body 112. In some embodiments, provisionally coupling cylindrical body 112 to resilient inserts 106 includes provisionally coupling cylindrical body 112 to bone fastener 108 or rod 104. In some embodiments, cylindrical body 112 may be provisionally coupled to resilient insert 106 with head 118 of bone fastener 108 in channel 151. Provisionally coupling cylindrical body 112, resilient insert 106 and bone fastener 108 may facilitate assembly of a spine stabilization system. The ability to advance cylindrical body 112, resilient insert 106 and bone fastener 108 at the same time may reduce surgery time during Minimally Invasive Surgery (MIS). In some embodiments, bone fastener 108 and resilient insert 106 may be cannulated to facilitate implantation. In some embodiments, cylindrical body 112 and one or more resilient inserts 106 may be provisionally coupled during manufacturing. Provisionally coupling cylindrical body 112 and one or more resilient inserts 106 may reduce the complexity of the surgery and may reduce risks associated with surgery.

In some embodiments, cylindrical body 112 may be provisionally coupled to second resilient insert 106 with rod 104 in channel 151. Provisionally coupling cylindrical body 112, second resilient insert 106 and rod 104 may facilitate assembly of a spine stabilization system. In some embodiments, cylindrical body 112, second resilient insert 106 and rod 104 may be provisionally coupled and cylindrical body 112 or second resilient insert 106 may be engaged by a tool and advanced into cylindrical body 112 coupled to bone fastener 108 engaged in a vertebral body.

Figure 6A:
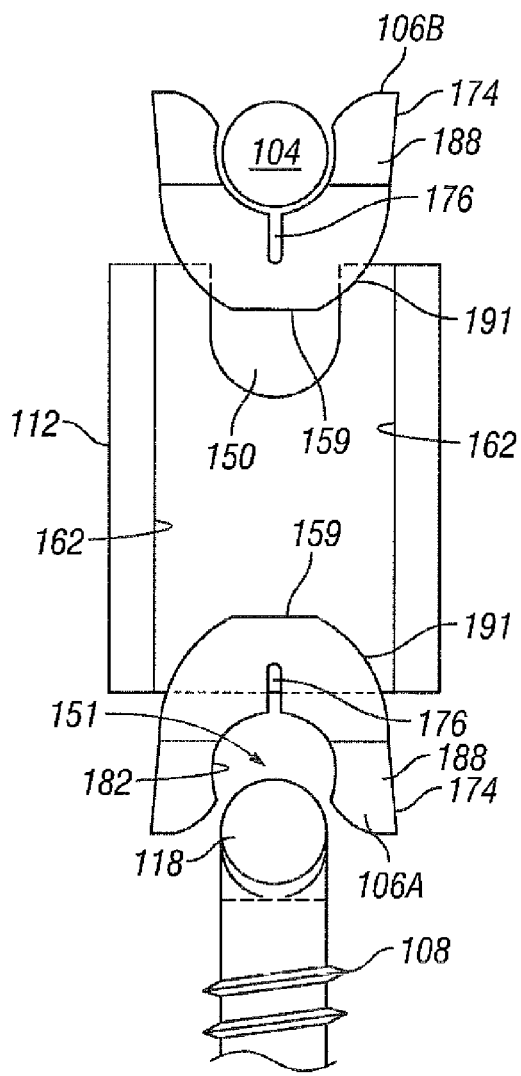
FIGS. 6A and 6B depict cross-section views of a portion of one embodiment of a spine stabilization system.
Figure 6B:
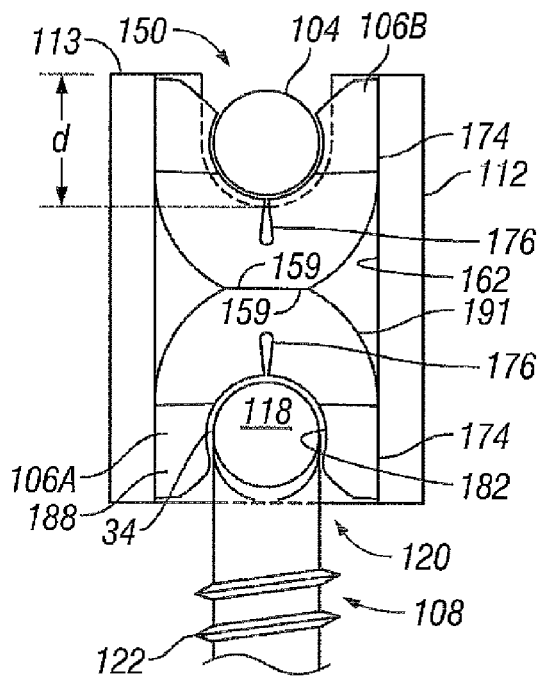

FIGS. 6A and 6B depict cross-section views of a portion of one embodiment of bone fastener assembly 102 and rod 104. FIG. 6A depicts an exploded cross-section view of bone fastener 108 and rod 104. Bone fastener assembly 102 may include bone fastener 108, first resilient insert 106A and second resilient insert 1068 and cylindrical body 112. First resilient insert 106A may be identical to second resilient insert 106B or may be different for optimal coupling with head 118 of bone fastener 108. In some embodiments, bone fastener 108 may engage a vertebral body (not shown).

First resilient insert 106A may be positioned on head 118 of bone fastener 108. Inner surface 182 of channel 151 may be textured, grooved or otherwise machined to inhibit movement of cylindrical body 112 relative to resilient insert 106 coupled to bone fastener 108. Head 118 of bone fastener 108 may be textured, grooved or otherwise machined to inhibit movement of bone fastener 108 relative to resilient insert 106. In some embodiments, resilient insert 106 may be frictionally inhibited from moving relative to head 118 of bone fastener 108. In some embodiments, resilient inserts 106 may accommodate heads 118 having various diameters or sizes. In some embodiments, head 118 may be sized such that portions of resilient inserts 106 do not contact neck 120 of bone fastener 108.

Cylindrical body 112 may be positioned over first resilient insert 106. In some embodiments, cylindrical body 112 may be positioned over first portion 191 of first resilient insert 106. Cylindrical body 112 may be advanced onto first resilient insert 106A. Inner surface 162 of cylindrical body 112 may compress deflectable arms 188 of first resilient insert 106A to decrease the width of channel 151 to capture head 118 of bone fastener 108. Inner surface 162 of cylindrical body 112 may collapse slot 176 of first resilient insert 106A to decrease the width of channel 151 to capture head 118 of bone fastener 108. Surface 34 of head 118 of bone fastener 108 may be frictionally inhibited from moving relative to inner surface 182 of resilient insert 106A. Inner surface 162 may have frictioned contact with surface 174 of first resilient insert 106A to inhibit first resilient insert 106A from withdrawing from cylindrical body 112.

Second resilient insert 106B may be advanced into cylindrical body 112. In some embodiments, second resilient insert 106 may have first portion 191 positioned in cylindrical body 112. Inner surface 162 of cylindrical body 112 may be textured, grooved or otherwise machined to inhibit movement of cylindrical body 112 relative to second resilient insert 106B coupled to rod 104. Outer surface 174 of second resilient insert 106B may be textured, grooved or otherwise machined to inhibit movement of cylindrical body 112 relative to second resilient insert 106B. In some embodiments, second resilient insert 106B may be frictionally inhibited from moving relative to cylindrical body 112. Slot 176 may be compressed during the advancement of cylindrical body 112 onto first resilient insert 106A.

Rod 104 may be positioned in channel 151 of resilient insert 106 and resilient insert 106 may be advanced into cylindrical body 112. Advancement of second resilient insert 106B into cylindrical body 112 may compress slot 176 to capture rod 104 in channel 151. Advancement of second resilient insert 106B into cylindrical body 112 may deflect deflectable arms 188 to capture rod 104 in channel 151. Inner surface 162 may have frictioned contact with surface 174 of second resilient insert 1068 to inhibit second resilient insert 106B from withdrawing resilient insert 106B from cylindrical body 112.

Advancement of second resilient insert into cylindrical body 112 may position rod 104 in recessed portions 150. Recessed portions 150 may have an associated depth d. Recessed portions 150 may provide additional support for rod 104. In some embodiments, advancement of first resilient insert 106A and second resilient insert 106B may contact bottom surfaces 159 of resilient inserts 106A and 106B.

Figure 7A:
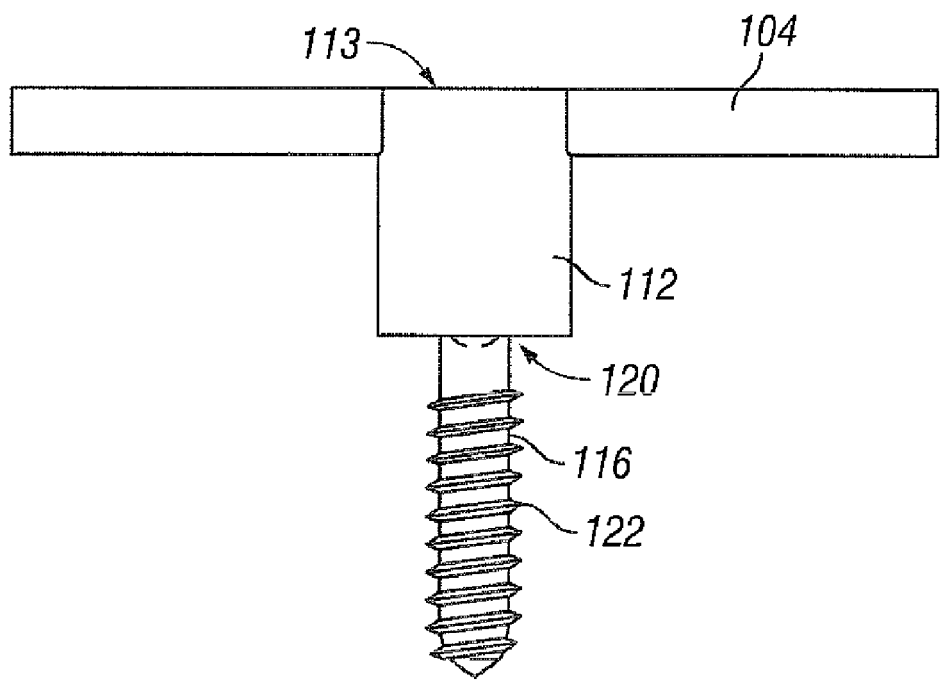
FIGS. 7A-7B depict side views of a portion of one embodiment of a spine stabilization system.
Figure 7B:
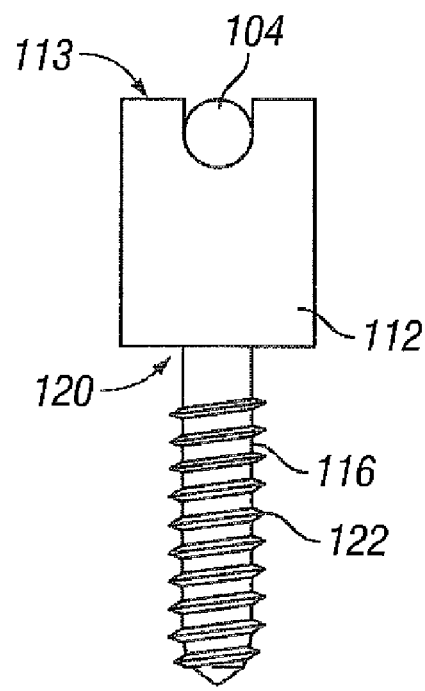

FIGS. 7A and 7B depict side views of one embodiment of a portion of spine stabilization system 100 having bone fastener 108 coupled to rod 104. In some embodiments, resilient insert 106 may be advanced into cylindrical body 112 until top surface 190 (as shown in FIG. 4B) is below top surface 113 of cylindrical body 112. In some embodiments, resilient insert 106 may be advanced into cylindrical body 112 until top surface 190 (as shown in FIG. 4B) is even with top surface 113 of cylindrical body 112. Advancing resilient insert 106 until top surface 190 is at or below top surface 113 of cylindrical body 112 may provide a surgeon with visual or tactile cues that resilient insert 106 is securely coupled to cylindrical body 112. In some embodiments, the position of top surface 190 relative to surface 113 may be determined visually. In some embodiments, the position of top surface 190 relative to surface 113 may be determined by tactile sensation. For example, in MIS procedures, or when resilient insert 106 is used to couple cylindrical body 112 to head of bone fastener 108, seeing resilient insert 106, surface 190 or surface 113 may be difficult. By using tactile sensations, either directly or through a tool, a surgeon can be sure that the assembled spine stabilization system 100 is securely coupled. In some embodiments, resilient insert 106 may be advanced into cylindrical body 112 until rod 104 is below top surface 113 of cylindrical body 112.

Various instruments may be used in a minimally invasive procedure to form a spinal stabilization system in a patient. The instruments may include, but are not limited to, positioning needles, guide wires, dilators, bone awls, bone taps, sleeves, drivers, tissue wedges, elongated member length estimating tools, mallets, tissue retractors, and tissue dilators. Embodiments disclosed herein may not require instruments that apply torques or countertorques to rod 104, cylindrical bodies 112, or resilient inserts 106. The instruments may be provided in an instrumentation set. The instrumentation set may also include components of the spinal stabilization system. The components of the spinal stabilization system may include, but are not limited to, bone fastener assemblies of various sizes and/or lengths, elongated members, and inserts.

A targeting needle may be used to locate an entry point in a vertebral body for a bone fastener of a bone fastener assembly. In some embodiments, the targeting needle may be a Jamshidi® bone marrow biopsy needle. A targeting needle may include an outer housing. The outer housing may include a hollow shaft and a handle. Scale markings printed, etched, or otherwise placed on the hollow shaft may be used to approximate a length of a bone fastener needed for a vertebra. The handle may provide a grip that allows a user to manipulate the targeting needle.

In some embodiments, a guide wire may be used to advance and/or position components at a placement site. The guide wire may be an 18-gauge K-wire. The guide wire may pass down a shaft of a targeting needle outer housing. A guide wire may be from about 15 cm to about 65 cm in length. In some embodiments, guide wires provided in an instrumentation set are about 46 cm in length. The length of a guide wire may allow a surgeon and/or assistants to hold at least one portion of the guide wire at all times when the guide wire is inserted into vertebral bone, even during insertion, use, and removal of instruments along a length of the guide wire. A guide wire that can be held continuously during a surgical procedure may inhibit removal or advancement of the guide wire from a desired position during a minimally invasive surgical procedure. A distal end of a guide wire may include a point, which may facilitate insertion of the distal end of the guide wire into vertebral bone. In some embodiments, a distal end of the guide wire may not be pointed. A position of an unpointed guide wire in bone may be easier to maintain during a spinal stabilization procedure.

Dilators may be used during a minimally invasive surgical procedure to push aside tissue and create space to access vertebral bone. In some embodiments, four tissue dilators of increasing diameter may be used to establish sufficient working space to accommodate instruments and spinal stabilization system components. In some embodiments, especially for a mid-vertebra or for mid-vertebrae of a multi-level stabilization system, only three dilators may be needed to form sufficient working space. Dilators in an instrumentation set may increase in diameter incrementally by a selected amount. For example, outside diameters of dilators in an instrumentation set may increase sequentially by increments of about 0.5 mm.

A bone awl may be used to breach cortical bone of a pedicle. A guide wire that is inserted in vertebral bone in a desired orientation may be inserted through a passage that extends through the bone awl. The bone awl may be moved down the guide wire so that the bone awl tip contacts the pedicle. The bone awl may have a length that allows a guide wire positioned in vertebral bone to always be held in at least one location when the guide wire is placed through a passage in the targeting needle.

During some surgical procedures downward force and some rotation of the bone awl may be sufficient to breach cortical of a vertebra. During some surgical procedures, an impact force may be needed for the bone awl to breach cortical bone. In some embodiments, a guide wire may be removed, the bone awl may be used to breach cortical bone, and the guide wire may be reinserted. In some embodiments, a small dilator may be placed over the portion of the guide wire extending from the bone awl so that a first end of the dilator contacts the bone awl. A mallet or other impact device may be used against a second end of the dilator so that the bone awl breaches cortical bone of the vertebra. The dilator may be removed from the bone awl and contact with the guide wire may be reestablished.

A bone tap may be used to form a threaded passage of a desired depth through a pedicle and into a vertebral body. The tap may have a passage so that the tap can be moved down the guide wire toward the bone.

A guide wire positioned in vertebral bone may be held near a top of a dilator inserted over the guide wire at a surgical site. A proximal end of the guide wire may be positioned through a distal end of a passage in the tap without a removable handle coupled to the shaft. A proximal portion of the guide wire may be held when the proximal portion of the guide wire extends beyond the top of the shaft. A portion of the guide wire may always be held during use of the tap. The shaft may be moved down the guide wire until the shaft contacts the vertebral bone.

A first reading of indicia relative to a proximal end of a dilator may be taken when a first flute is located at a pedicle. The tap may be rotated so that flutes form a threaded opening through the pedicle and into a vertebral body. The flutes may have a diameter that is about 0.1 mm to about 0.7 mm less than a maximum thread flight of a bone fastener to be positioned in the threaded opening formed by the flutes. In one embodiment, the tap may form a thread that is about 0.5 mm less than a maximum thread flight of a bone fastener to be positioned in the threaded opening formed by the flutes. A position of the tap may be monitored using a fluoroscope. When the threaded opening is formed to a desired depth, a second reading of indicia relative to the dilator may be taken. A length of a bone fastener to be inserted into the vertebral body may be estimated by taking the difference between the indicia readings. After a threaded opening is formed to a desired depth, the tap may be removed by rotating the tap until all the flutes are disengaged from the vertebral bone.

A detachable member may be used as a guide to install bone fasteners 108 of a spine stabilization system in vertebral bone. A detachable member may be coupled to bone fastener 108. A distal end of a detachable member may be tapered or angled to reduce bulk at a surgical site. A cross section transverse to a longitudinal axis of a detachable member may have shapes including, but not limited to, circular, ovoid, square, pentagonal, hexagonal, and combinations thereof. In some embodiments, a detachable member may be hollow. In some embodiments, a thickness of a hollow detachable member may be uniform. In some embodiments, a thickness of a hollow detachable member may vary along the length of the detachable member. A detachable member with a passage extending longitudinally from a first end of the detachable member to a second end of the detachable member may be referred to as a "sleeve".

Instruments may be inserted into the sleeve to manipulate bone fastener 108. Movement of the sleeve may alter an orientation of cylindrical body 112 relative to bone fastener 108 of spine stabilization system 100. In some embodiments, a sleeve may be used as a retractor during a spinal stabilization procedure.

A sleeve for a single-level vertebral stabilization system may include one or more channels in a wall of the sleeve to allow access to an adjacent vertebra. For some single-level vertebral stabilization procedures, only single-channel sleeves (i.e., sleeves with a single channel in a wall of the sleeve) may be used. For other single-level vertebral stabilization procedures, one or more multi-channel sleeves (i.e., sleeves with two or more channels in a wall of the sleeve) may be used. Channels may provide flexibility to or enhance flexibility of a multi-channel sleeve. In some embodiments, a proximal portion of a multi-channel sleeve may have a solid circumference. A region of solid circumference in a multi-channel sleeve may enhance stability of the multi-channel sleeve. In some embodiments, a multi-channel sleeve may be longer than a single-channel sleeve.

A sleeve used at a middle vertebra in a multi-level stabilization procedure may be a multi-channel sleeve. Channels in a multi-channel sleeve may allow access to adjacent vertebrae from a middle vertebra. A sleeve used at an end vertebra of a multi-level stabilization system may be a single-channel sleeve or a multi-channel sleeve. A system for coupling a bone fastener assembly to a multi-channel sleeve may include a limiter that inhibits spreading of arms of the sleeve to inhibit release of the bone fastener assembly from the sleeve.

A channel in a wall of a sleeve may allow access to a vertebra that is to be stabilized with a spinal stabilization system being formed. In some embodiments, a single-channel sleeve may be coupled to a bone fastener assembly to be inserted into vertebral bone of a first vertebra. The single-channel sleeve may allow access to a second vertebra from the first vertebra. In some embodiments, a multi-channel sleeve may be coupled to a bone fastener assembly to be inserted into vertebral bone of a first vertebra. The multi-channel sleeve may allow access from the first vertebra to adjacent vertebrae.

Instruments may access a spine stabilization system through a passage in a sleeve. In some embodiments, a channel in a wall of a sleeve may extend a full length of the sleeve. In some embodiments, especially in embodiments of multi-channel sleeves, a channel in a wall of a sleeve may extend only a portion of the length of the sleeve. In some embodiments, a channel in a wall of a sleeve may extend 25%, 50%, 75%, 80%, 90%, 95% or more of the length of the sleeve. A channel may extend to a distal end of a sleeve such that a rod inserted in the channel may pass from the sleeve into a slot of a cylindrical body of a bone fastener assembly coupled to the sleeve.

A channel in a sleeve may be any of a variety of shapes. A channel may have a width that exceeds a width (e.g., a diameter) of a rod that is to be inserted in the channel. In some embodiments, a channel may be a linear opening parallel to a longitudinal axis of the sleeve. In some embodiments, a channel may have a non-linear shape including, but not limited to, a helical pattern, an arc, an "L" shape, or an "S" shape. A non-linear channel may allow a rod to travel along a predetermined path. In some embodiments, adjacent sleeves may include channels with matching profiles, allowing ends of a rod to follow similar paths down the sleeve channels.

In some embodiments, a sleeve may be a multi-channel sleeve having walls forming a passage, and channels that extend from a distal end of the sleeve through a portion of the walls. Channels in the walls may allow instruments to be positioned and used to form a plane through soft tissue to one or more adjacent vertebrae. A rod may be inserted in the tissue plane and positioned in cylindrical bodies of bone fastener assemblies anchored in vertebrae and coupled to sleeves. A passage may allow instruments to be positioned and used to manipulate a bone fastener assembly that is coupled to a distal end of the sleeve. A distal end of a sleeve may include a flange that mates with a complementary flange on a cylindrical body of a bone fastener assembly. A distal end of a sleeve may be tapered to reduce bulk (e.g., reduce spin diameter) at a surgical site.

In some embodiments, a sleeve may be a single-channel sleeve for use in single-level or multi-level spinal stabilization procedures. A sleeve may be used at the outermost vertebrae to be stabilized during installation of a multi-level vertebral stabilization system. The sleeve may be coupled to a cylindrical body of a bone fastener assembly. Instruments may be inserted through a passage in the sleeve to access an anchored bone fastener assembly coupled to the sleeve. An instrument may be moved through a channel toward an adjacent vertebra to form a tissue plane in soft tissue between the sleeve and the adjacent vertebra.

A sleeve may be coupled to a bone fastener assembly in various ways to inhibit movement of the sleeve relative to a cylindrical body of the bone fastener assembly. A system used to couple the sleeve to the bone fastener assembly may inhibit rotation and translation of the sleeve relative to the cylindrical body.

A sleeve may be coupled to a cylindrical body of a bone fastener assembly in various ways. When a sleeve is coupled to a cylindrical body, rotation and translation of the sleeve relative to the cylindrical body may be inhibited. A system used to couple a sleeve and cylindrical body should be simple, inexpensive to implement, and should not significantly weaken the mechanical strength of the cylindrical body and/or the sleeve. Sleeves may be coupled to cylindrical bodies using various coupling systems including, but not limited to, flanges, threaded connections, interlocking connections (e.g., ratcheting connection systems), and/or interference fits.

In one embodiment of an interlocking connection system, a sleeve may include an opposing pair of deflectable arms. Each deflectable arm may include a tooth. The deflectable arms may be forced outwards during coupling of a cylindrical body to the sleeve. When the cylindrical body is coupled to the sleeve, the deflectable arms may be positioned in channels in the cylindrical body, with the teeth positioned in indentations in the cylindrical body. The presence of the deflectable arms in the channels of the cylindrical body may inhibit rotation and translation of the sleeve relative to the cylindrical body. Separation of the sleeve from the cylindrical body may be achieved by insertion of an expander in the sleeve. The expander may be used to force the deflectable arms outwards and expel the teeth from the indentations.

In some sleeve and cylindrical body coupling embodiments, the sleeve and the cylindrical body may include members that work together to inhibit radial expansion of walls of the sleeve. A stop in a sleeve and a ledge in a cylindrical body may be needed in a multi-channel sleeve embodiment. A stop in a sleeve and/or a ledge in a cylindrical body may not be needed in a single-channel sleeve embodiment or in a cylindrical body for single-level stabilization.

In some sleeve and cylindrical body coupling embodiments, a sleeve may include a protrusion that mates with a complementary groove in a cylindrical body. Alternatively, a sleeve may include a groove that mates with a complementary protrusion of a cylindrical body.

In some embodiments, a sleeve and/or a cylindrical body may include a locking system to inhibit rotation of the sleeve relative to the cylindrical body. The locking system may be, but is not limited to, threading, interference fits, frictional engagement, or a press-fit connection. In some embodiments, a locking system may inhibit translation and/or rotation of a sleeve relative to a cylindrical body.

In one embodiment in which distal end portions of movable members in a sleeve are threaded and openings in the cylindrical body are threaded, rotation and translation of the cylindrical body relative to the sleeve may be inhibited when distal end portions of the movable members are positioned in the openings.

In one embodiment, an inner sleeve may be positioned in a sleeve to inhibit translation and/or rotation of the sleeve relative to a cylindrical body of a bone fastener assembly. A distal end of inner the sleeve may contact an upper end of cylindrical body 112. A proximal portion of the inner sleeve may engage a proximal portion of the sleeve. The engagement may allow the inner sleeve to apply a force against cylindrical body 112 that presses a flange against a flange on the sleeve to inhibit translation of the sleeve relative to the cylindrical body. The engagement may be, but is not limited to, a threaded connection, an interference fit, a frictional fit, or a keyway type of connection.

In some embodiments, a distal end of an inner sleeve may be roughened or textured to frictionally engage a proximal surface of the cylindrical body. The frictional engagement may inhibit rotation of the sleeve relative to the cylindrical body.

In some embodiments, a sleeve may include a pair of hinged arms configured to couple to a cylindrical body. The arms may be pivotally coupled together by a hinge located near a proximal end of a sleeve. In some sleeve embodiments, a sleeve may include a locking element or a biasing element (e.g., a spring) near or at the hinge. A locking element or biasing element may cause a clamping force to be exerted on the cylindrical body to maintain the cylindrical body in the sleeve and/or to inhibit rotation of the cylindrical body in the sleeve.

In some sleeve embodiments, proximal portions of sleeves may be chamfered to allow ends of the sleeves to more closely approach each other than sleeves with a uniform cross section. Chamfered surfaces may reduce space between proximal ends of two sleeves. During some surgical procedures, only one of the sleeves may be chamfered. During some surgical procedures, the use of a sleeve with a chamfered surface may allow for a smaller incision than required when using non-chamfered sleeves. In some embodiments, other types of sleeves may be used to reduce space between proximal ends of sleeves. Other types of sleeves may include, but are not limited to, sleeves of different lengths, sleeves of different diameters, and sleeves with flexible end portions.

Sleeves may be of various lengths. Sleeves of different lengths may be used in the same surgical procedure. A sleeve length used in a spinal stabilization procedure may be determined by a patient's anatomy. Sleeves may be just short enough to allow manipulation by a medical practitioner above an incision in a patient. In some embodiments, sleeves may be about 3.5 to about 11.5 cm long. For example, a single-channel sleeve may be about 10 cm long. In some embodiments, sleeves may be about 11.5 cm to about 14 cm long. For example, a single-channel or a multi-channel sleeve may be about 12.5 cm long. A multi-channel sleeve may be longer than a single-channel sleeve. In some embodiments, a multi-channel sleeve may be at least about 15 cm long. For example, a multi-channel sleeve may be about 16 cm long. Sleeves that are too long may require a longer incision and/or a larger tissue plane for insertion of a spinal stabilization system. Insertion of a rod may be more difficult with sleeves that are longer than necessary. Sleeves with excess length may be bulky and hard to manipulate during a surgical procedure.

A sleeve may be flexible over its entire length or include a flexible portion near a proximal end of the sleeve. A flexible portion may allow positioning of a proximal portion of a sleeve in a desired location. A flexible portion may be produced from any of various materials including, but not limited to, a surgical grade plastic, rubber, or metal. A flexible portion may be formed of various elements, including, but not limited to, a tube, a channel, or a plurality of linked segments.

During some spinal stabilization procedures, a sleeve without a second portion that is able to move relative to a first portion may be used at one vertebra, and a sleeve with a second portion that is able to move relative to a first portion may be used at one or more vertebrae that are to be stabilized.

When bone fasteners of polyaxial bone fastener assemblies are positioned in vertebral bone, sleeves coupled to cylindrical bodies of the bone fastener assemblies may be moved in desired positions. During surgery, a sleeve in a patient may be oriented towards an adjacent vertebra that is to be stabilized to reduce the required incision size. In some embodiments, channels of the sleeves may be aligned so that a rod may be advanced into resilient inserts positioned in cylindrical bodies of the bone fastener assemblies. In some embodiments, multi-channel sleeves may be coupled to all three pedicles. In some embodiments, differently shaped sleeves (e.g., circular, oval) may be used in one or more of the pedicles. Channels of the sleeves may be aligned so that a rod may be moved down the sleeves and into resilient inserts and advanced into the cylindrical bodies of the bone fastener assemblies.

In some embodiments, channels of sleeves may face a direction other than toward each other. A rod may be curved in an appropriate shape to engage slots in the cylindrical bodies when the channels of the sleeves are angled. In some embodiments, channels in the sleeve may not be longitudinal channels down the length of the sleeve. In embodiments of sleeves with non-longitudinal channels, the channels of two adjacent sleeves may not face towards each other when the openings of cylindrical bodies coupled to the sleeves are aligned.

In one embodiment, a frame may couple to two or more sleeves. As used herein, a "frame" includes any of a variety of structural elements including, but not limited, rods, bars, cages, or machined blocks. In some embodiments, a frame may provide a rigid coupling between two sleeves. In some embodiments, a frame may allow for angular or translational movement between sleeves. For example, in some embodiments a frame may include slidable elements that allow sleeves to be translated toward each other or away from each other to facilitate compression or distraction of vertebrae. In some embodiments, a frame may enable sleeves to pivot toward each other or away from each other. In some embodiments, a frame may allow for movement of sleeves to facilitate spinal reduction.

In some embodiments, after a bone fastener assembly is coupled to a sleeve, a driver may be coupled to a bone fastener of the bone fastener assembly. The driver may be used to insert the bone fastener into vertebral bone. In some embodiments, a driver may be positioned in a sleeve and coupled to bone fastener 108 and/or cylindrical body 112. Coupling the driver to cylindrical body 112 and to bone fastener 108 may ensure proper alignment of the driver relative to bone fastener 108. Coupling the driver to cylindrical body 112 and to bone fastener 108 may also inhibit movement of the cylindrical body relative to the bone fastener during insertion of the bone fastener.

A driver may be positioned in a passage in a sleeve and coupled to a bone fastener during use. The driver may be rotatable relative to the sleeve so that a bone fastener can be inserted into vertebral bone. In some embodiments, clearance between the driver and the sleeve may be relatively small. In some embodiments, the clearance between the driver and the sleeve may range from about 0.1 mm to about 0.75 mm. For example, the clearance between the driver and the sleeve may be about 0.25 mm (i.e., an inner diameter of the sleeve may be about 0.5 mm greater than an outer diameter of the driver). Also, clearance between a sleeve and a dilator may be relatively small. The small clearances may inhibit undesired movement of the instruments relative to each other and/or reduce bulkiness at the surgical site.

During a minimally invasive surgical procedure, a plane may be created in tissue from a first vertebra to a second vertebra. A rod may be positioned in the plane during the surgical procedure. In some embodiments, a tissue plane may be formed using a targeting needle. The targeting needle may be positioned at the first vertebra. The distal end of the needle may be moved toward the second vertebra to form the plane while maintaining a position of the needle at a surface of the skin. The needle may be moved back and forth a number of times to clearly establish the plane. Care may need to be taken to avoid bending the targeting needle during establishment of the plane.

In some embodiments, a tissue wedge may be used to form a plane in tissue between a first vertebra and a second vertebra. A blade used in a wedge may be a double-wedged blade, may have a diamond-like shape, may have blunt edges to avoid severing tissue during use of the tissue wedge, or the like. The distal end of a blade may be rounded. A shape of the distal end may inhibit damage to tissue and may facilitate movement of the blade towards a target location during formation of a plane in tissue between vertebrae. In some tissue wedge embodiments, a tissue wedge may include a hook. A cutting edge in the hook may be used to sever portions of tissue (e.g., fascia) through which a blade cannot form a plane. A cutting edge may be oriented in the blade so that severing of tissue results when the tissue wedge is pulled away from the spine.

An estimating tool may be used to estimate a distance between bone fastener assemblies anchored in vertebrae. The bone fastener assemblies may be part of a single-level or multi-level spinal stabilization system. The distance estimated by an estimating tool may be used to determine a desired length of a rod to be coupled to the anchored bone fastener assemblies. An estimating tool may be designed such that a maximum separation distance exceeds an expected distance between anchored bone fastener assemblies. Fully extended arms may be manually compressed and inserted into passages of sleeves coupled to anchored bone fastener assemblies. For a multi-level system, the arms may be inserted in sleeves coupled to the outermost bone fastener assemblies while one or more sleeves coupled to one or more inner vertebrae are held out of the way.

An estimating tool may be advanced toward anchored bone fastener assemblies. In some embodiments, an estimating tool may be advanced toward the anchored bone fastener assemblies until members of the estimating tool contact cylindrical bodies and/or bone fasteners of the bone fastener assemblies. With the estimating tool contacting cylindrical bodies and/or bone fasteners, an activator of the estimating tool may be engaged. Engaging an activator of an estimating tool may limit the biasing element such that the distance between the members of the estimating tool does not exceed the distance between the anchored bone fastener assemblies. With the activator engaged and the distance between the members of the estimating tool fixed to indicate the distance between the anchored bone fastener assemblies, the estimating tool may be moved upwards to remove the estimating tool from the patient. When the estimating tool is moved upwards, arms may compress to facilitate removal of the estimating tool from the sleeves.

Once removed from the sleeves, the biasing element may restore the distance between the members of the estimating tool to indicate the separation between anchored bone fastener assemblies 102. The distance between the members of the estimating tool may be used to estimate a length of rod 104 needed to couple the anchored bone fastener assemblies 102. The distance may be read using a scale provided in the instrumentation kit. In some embodiments, the scale may be indicia or etching on a surface of the instrumentation kit. In one embodiment, a length of rod 104 may be chosen to allow for bending of rod 104 and/or to allow rod 104 to extend beyond cylindrical bodies 112 of the anchored bone fastener assemblies 102. For example, 15 mm may be added to the distance between the members of the estimating tool. In some embodiments, a length of rod 104 may be chosen such that rod 104 extends 2 mm or more beyond cylindrical bodies 112. In some embodiments, a length of rod 104 may be chosen such that ends of rod 104 do not extend from cylindrical bodies 112.

In some embodiments, an estimating tool may include a gage having arms for providing an estimate of the distance between sleeves. Thus, with the arms of the estimating tool positioned together, the gage may have or may be set to a zero reading. With the arms extended to meet resistance in the sleeves, the gage may provide an estimate of the distance between the sleeves. The distance between the sleeves may be used to estimate a length of rod 104 needed to couple the anchored bone fastener assemblies. In one embodiment, a length of rod 104 may be chosen to be greater than the distance measured by a gage to allow rod 104 to extend beyond slots of cylindrical bodies 112 of anchored bone fastener assemblies 102.

In some embodiments, a rod positioner may be used to guide rod 104 through one or more sleeves coupled to bone fastener assemblies 102 and to position rod 104 in resilient inserts 106 advanced into cylindrical bodies 112 proximate pedicles of vertebrae. A rod positioner may include an outer shaft, a handle, an inner shaft, and a grasping member. In some embodiments, the grasping member may be a hook. A first end (i.e., proximal end) of the outer shaft may be connected to the handle. A second end (i.e., distal end) of the outer shaft may be coupled to the grasping member. The inner shaft may pass through the handle and the outer shaft. A second end (i.e., a distal end) of the inner shaft may contact rod 104 positioned in the grasping member. A first end (i.e., proximal end) of the inner shaft may extend from the handle. The proximal end of the inner shaft may be a knob or a thumb plate. An amount of force applied to a rod positioned between the grasping member and the distal end of the inner shaft may be controlled by the amount of pressure applied to the proximal end of the inner shaft. Pressure may be applied to the proximal end of the inner shaft manually or mechanically. Mechanical means of applying pressure to the proximal end of the inner shaft include, but are not limited to, forceps handles and an adjustable rotor. The distal end of the inner shaft may be positioned proximate a grasping member. Rod 104 may be positioned between the grasping member and the distal end of the inner shaft of the positioning tool before or after initial insertion of rod 104 into a sleeve. Rod 104 may be held between the grasping member and the distal end of the inner shaft with pressure applied to the proximal end of the inner shaft. The distal end of the inner shaft may be contoured (e.g., curved) to allow some motion (e.g., rocking motion) of rod 104 while rod 104 is coaxed into position. During some installation procedures, a positioning tool may remain coupled to rod 104 until resilient inserts 106 are secured in cylindrical bodies 112 of anchored bone fastener assemblies 102. In some cases, pressure supplied to rod 104 with a rod positioner may not be sufficient to seat rod 104 in resilient insert 106 in cylindrical body 112. A seater may be used in conjunction with a rod positioner to maneuver rod 104 into one or more resilient inserts 106 in cylindrical bodies 112. During some procedures, a rod positioner may be removed from rod 104 before using the seater. After rod 104 has been positioned and seated in resilient inserts 106 as desired, resilient inserts 106 may be advanced into cylindrical bodies 112 to secure rod 104 to cylindrical bodies 112.

Minimally invasive procedures may involve locating a surgical site and a position for a single skin incision to access the surgical site. The incision may be located above and between (e.g., centrally between) vertebrae to be stabilized. An opening under the skin may be enlarged to exceed the size of the skin incision. Movement and/or stretching of the incision, bending of a rod, and angulation of cylindrical bodies of bone fastener assemblies may allow the length of the incision and/ or the area of a tissue plane to be minimized. In some embodiments, minimally invasive insertion of a spinal stabilization system may not be visualized. In some embodiments, insertion of a spinal stabilization system may be a top-loading, mini-opening, muscle-splitting, screw fixation technique.

Insertion of a spinal stabilization system may include gradually increasing the diameter of an opening formed in a pedicle and/or vertebral body to accept a bone fastener assembly. For example, a targeting needle may have outer diameter of about D. A bone awl inserted after the targeting needle may have an outer diameter incrementally larger than the outer diameter of the targeting needle. As used herein, an incrementally larger diameter may be large enough to allow a snug but adjustable fit. For example, the bone awl may have outer diameter of about (D+x). A tap portion of a bone tap inserted after the bone awl may have a minor diameter of about (D+2x). A bone fastener may have a minor diameter of about (D+3x). In some embodiments, x may be between about 0.1 mm and about 1.0 mm. For example, x may be about 0.5 mm. Incremental sizing of the targeting needle, bone awl, tap, and bone fastener may promote a proper fit of the bone fastener in the vertebra to be stabilized.

In one embodiment of a spinal stabilization system insertion method, the patient may be placed in a prone position on a radiolucent table with clearance available for a C-arm of a fluoroscope. For example, a Jackson table with a radiolucent Wilson frame attachment may be used. The ability to obtain high quality images is very important. Bolsters, frames, and pads may be inspected for radiolucency prior to the operation. Placing the patient in a knee-chest position (e.g., using an Andrews table) should be avoided. Care should be taken to avoid placing the patient's spine in kyphosis during positioning of the patient.

The C-arm of the fluoroscope should be able to freely rotate between the anteroposterior, lateral, and oblique positions for optimal visualization of pedicle anatomy during the procedure. The arm should be rotated through a full range of motion prior to beginning the procedure to ensure that there is no obstruction or radio-opaque object in the way. The fluoroscope may be positioned so that Ferguson views and "bullseye" views are obtainable. Once the patient is positioned and the ability to obtain fluoroscopic images of the target levels for instrumentation has been confirmed, the patient may be prepared and draped sterilely.

For most of the lumbar region, the vertebral pedicle is an obliquely oriented cylindrical corridor. The angulation varies by approximately 5 degrees per level (e.g., L1: 5 degrees; L5: 25 degrees). A pre-operative fine-cut computed tomography image may be examined to determine any unique anatomy of the patient. Acquiring the pedicle in the most lateral and superior quadrant of the pedicle may be desirable to avoid the overriding facet during a minimally invasive procedure. A lateral entry point may allow for better screw convergence as well as less interference with the superior adjacent level facet joint. A targeting needle may be passed in a medial and inferior trajectory, thus following the natural pathway of the pedicle. Frequent fluoroscopic inspection in both an anteroposterior and lateral plane may ensure proper passage of the needle as the needle is inserted into vertebral bone.

Various techniques may be used to plan the skin incisions and entry points. In one embodiment, the planning sequence for a single-level stabilization may include the following four steps. First, an anteroposterior image may be obtained with the spinous processes centered at the target vertebral bodies. Vertical lines passing through midpoints of pedicles that are to receive bone fasteners may be marked on the patient. The lines do not represent skin entry points. The lines are markers of pedicle entry points used to estimate angles at which targeting needles to be inserted to contact the pedicles. In some embodiments, sets of vertical lines may be drawn corresponding to the lateral edges of the pedicles instead of lines corresponding to the midpoints of the pedicles.

Second, horizontal lines may be marked approximately through the centers of the pedicles (mid-pedicle lines) on the patient. In some embodiments, the lines may be drawn on the superior side of the center axes (superior to the mid-pedicle).

Third, an oblique or "bullseye" view (i.e., down a longitudinal axis of a pedicle) may be obtained on each side of the patient for each pedicle that is to be stabilized. Vertical oblique view lines may be marked on the skin at the midpoints of each of the pedicles that are to receive a bone fastener. The oblique view lines may be drawn in a different color than the vertical lines drawn during the first step. In some embodiments, vertical lines may be drawn corresponding to the lateral edges of the pedicles instead of lines corresponding to the midpoints of the pedicles.

The oblique view lines may be about 2 cm to about 3 cm away from the lateral pedicle border lines marked in the first step. For larger patients, the oblique view line may be greater than about 3 cm away from the midline marked in the first step. For smaller patients, the oblique view line may be closer than about 2 cm away from the midline marked in the first step. The intersection of the oblique view lines with the horizontal lines drawn in the second step may represent skin entry points for a targeting needle as the targeting needle passes through soft tissue at an angle towards the bony pedicle entry point. A side fluoroscopic image, the horizontal lines, and the vertical lines may help the surgeon triangulate between the skin entry points and bony entry points.

Fourth, an incision may be made in the skin between mid-pedicle lines along the vertical oblique view lines. The skin incision may be from about 2 cm to about 4 cm long. In some embodiments, the incision may be from about 2.5 cm to about 3 cm long. Limiting the length of the incision may enhance patient satisfaction with the procedure. The incisions may be pre-anesthetized with, for example, 1% lidocaine with 1:200, 000 epinephrine. To blunt the pain response, a long spinal needle may be used to dock on the bone entry point and inject the planned muscle path in a retrograde fashion as well. Once the incision has been made, tissue surrounding the incision may be pulled and/or stretched to allow access to a target location in a vertebra.

After sterile preparation and draping, the pedicle entry points may be fluoroscopically rechecked to ensure that the previously marked lines correspond to the intersection of the midline of the transverse process and the lateral joint and pars interarticularis. The intersection of the facet and the transverse process provides a starting point that may help avoid the canal and follow the natural inclination of lumbar pedicles. For the spinal stabilization system described, in which sleeves coupled to bone fastener assemblies are substantially unconstrained by insertion angles of the bone fasteners, patient anatomy may determine the most advantageous insertion angles of the bone fasteners.

A scalpel may be used to make a stab wound at the junction of an oblique view line and a mid-pedicle line. In one embodiment, the scalpel may be a #11 scalpel. A targeting needle may be passed through the incision in an oblique lateral to medial trajectory towards the bony entry point defined by a lateral pedicle border line. The C-arm of the fluoroscope may be placed in an anteroposterior position for this maneuver.

As the targeting needle encounters the bony anatomy, anteroposterior fluoroscopic images may be used to place the tip of the needle at the upper outer quadrant of the pedicle. In some embodiments, the needle may be walked medially along the transverse process to the pedicle entry point. In some embodiments, the needle tip may be docked by lightly tapping the tip into the bone with a mallet or other impact device to drive the tip into the bone. In some embodiments, the needle tip may be docked by applying downward pressure to the targeting needle to force the tip into the bone.

The fluoroscope may then be moved to a lateral position. The surgeon may correct the sagittal trajectory of the needle by moving the needle in an anterior or posterior direction to match the vector of the pedicle corridor. In some embodiments, a mallet or other impact device may be used to gently advance the targeting needle into the pedicle halfway to the pedicle-vertebral body junction. In some embodiments, force may be applied to the targeting needle to drive the targeting needle into the pedicle halfway to the pedicle-vertebral body junction. An anteroposterior image may then be obtained to confirm that the needle is approximately halfway across the pedicle in the anteroposterior view. If the tip is more than halfway across the pedicle in a lateral to medial projection, the trajectory may be too medial. Further advancement of the needle may risk passing the needle through the spinal canal. The needle may be repositioned. A new starting point or new trajectory may be obtained. If the anteroposterior image demonstrates that the needle is significantly lateral in the pedicle, then the needle may have passed along the lateral portion of the pedicle. A needle that has passed along the lateral portion of the pedicle may be withdrawn and repositioned.

Once a proper trajectory has been obtained, the targeting needle may be advanced using a mallet. In some embodiments, the needle may be pushed in without a mallet. The targeting needle may be advanced to the junction of the pedicle and vertebral body under lateral fluoroscopic guidance. At this point, confirmation of position and trajectory can be repeated under anteroposterior fluoroscopy. A scale on the targeting needle may be used to approximate a length of a bone fastener to be used. A first depth of the targeting needle may be measured relative to a body surface when a pedicle is first encountered. A second depth of the targeting needle may be measured relative to the body surface after the targeting needle has been advanced to the desired depth in the vertebral body. An approximate length of the pedicle screw to be used may be determined by taking a difference between the depth measurements.

After the targeting needle is in a proper position, a guide wire may be placed through a passage in the targeting needle into the vertebral body. Lateral fluoroscopic images may be obtained to indicate the position of the guide wire. In some embodiments, a small diameter tissue dilator may be placed over the guide wire and positioned on an upper surface of the targeting needle. The tissue dilator may provide stability to the guide wire. Added stability from the dilator may allow the guide wire to be successfully tapped into the vertebral body with a small mallet. Care should be taken to avoid kinking the guide wire.

Once the guide wire has been passed through the targeting needle and the targeting needle has been removed, the guide wire may be used as a guide to position one or more successively sized dilators around a target location in a pedicle. A dilator may be a conduit with a regular shape (e.g., cylindrical) or an irregular shape (e.g., C-shaped). A dilator may form an opening through soft tissue to the pedicle. For patients with a thick fascia, it may be advantageous to make a nick in the fascia with a scalpel blade to facilitate passage of the dilators. The dilators may be passed sequentially over the guide wire. The dilators may be rotated during insertion to facilitate dilation of surrounding tissue. The dilators may be inserted until the leading edges contact the pedicle. A distal end of a dilator may be tapered to facilitate positioning of the dilator proximate the pedicle. An instrumentation set for a spinal stabilization system may include two, three, four, or more successively sized dilators.

Successively sized dilators may have an inner diameter just slightly larger than an outer diameter of another dilator. In some embodiments, successively sized dilators may have an inner diameter that is between about 0.03 mm and about 1.0 mm greater than the outer diameter of another dilator. For example, an inner diameter of a first dilator may be about 0.5 mm greater than the outer diameter of the guide wire. Lengths of dilators in a successively sized set may decrease with increasing diameter to facilitate removal of the smaller dilators. Care should be taken to avoid dislodging the guide wire during insertion and removal of the dilators.

After tissue dilation has been achieved, a large diameter dilator may be used to guide bone fastener assembly 102 including bone fastener 108, first resilient insert 106, cylindrical body 112 and/or insertion instruments toward a target location in a pedicle. In some embodiments, bone fastener assembly 102 includes bone fastener 108, first resilient insert 106, cylindrical body 112 and second resilient insert 106.

In some embodiments, a pedicle may be prepared for receiving a bone fastener assembly. A bone awl may be positioned such that a tip of the bone awl is on or near a surface of a pedicle. The bone awl may be driven downwards into the pedicle to breach cortical bone of the pedicle. After the pedicle is breached, the bone awl may be removed from the patient. In some embodiments, an initial passage may be formed in the pedicle and the vertebral body using a drill or a drill and tap combination. A tap may be rotated to form a threaded passage through a pedicle and into a vertebral body to a desired depth. In some embodiments, a length of the threaded portion of a tap may be used to determine a depth of a threaded passage formed in a bone. For a threaded portion of a known length (e.g., 30 mm, 45 mm, 60 mm), a scaled image (e.g., X-ray image) of a depth of the threaded portion in a bone monitored during tapping may allow a medical practitioner to determine the depth of the threaded passage. In some embodiments, a tap may form threads of major diameter about 0.5 mm smaller than a major diameter of threads of bone fastener 108 to be inserted into the threaded passage.

In some embodiments, bone fastener assembly 102 with bone fastener 108 of an appropriate length may be selected for insertion in a patient. The size of bone fastener 108 may be verified with measurement indicia in an instrumentation set. In some embodiments, measurement indicia may be etched or printed on a portion of an instrumentation set. For example, the chosen bone fastener embodiment may be placed over the outline of bone fastener 108 embodiment printed on a tray of the instrumentation set.

The chosen bone fastener assembly 102 may be attached to a tool. In one embodiment, bone fastener assembly 102 may be rotated on a flange of a sleeve (not shown). A driver may be used to extend the movable members to couple with cylindrical body 112. When bone fastener assembly 102 is coupled to the sleeve, a drive portion of a driver may be coupled to bone fastener 108. A shaft of the driver may be positioned in the passage of the sleeve. A removable handle may be attached to the shaft of the driver. The sleeve, cylindrical body 112, first resilient insert 106 and bone fastener 108 may be substantially co-axial when the fastener driver is positioned in the sleeve. In some embodiments, the removable handle may be attached to the shaft of the driver after the bone fastener 108, cylindrical body 112, resilient insert 106, sleeve, and fastener driver combination is positioned down a guide wire through a dilator and against a pedicle.

After insertion of bone fastener assembly 102, sleeve, and driver in a dilator, the driver may be rotated to thread bone fastener 108 into the pedicle 164 and vertebral body. Bone fastener 108 may be advanced into the pedicle under fluoroscopic guidance to inhibit breaching of the pedicle walls. When the tip of bone fastener 108 advances beyond the posterior margin of the vertebral body, the guide wire may be removed to inhibit inadvertent bending of the guide wire or unwanted advancement of the guide wire. Bone fastener 108 may be advanced to the facet joint. Bone fastener 108 may then be backed off about a quarter of a turn. Backing bone fastener 108 off about a quarter of a turn may allow for full motion of cylindrical body 112 relative to bone fastener 108. After bone fastener 108 has been advanced to the desired depth, the driver may be removed from the head of bone fastener 108 and from the patient.

After bone fastener 108 has been secured to the vertebra and the driver has been removed from the sleeve, the rotational capabilities of cylindrical body 112 provisionally coupled to resilient insert 106 and bone fastener 108 may allow angulation of the sleeve relative to bone fastener 108. Tissue surrounding the incision may be released such that the sleeve is angled toward a central location between vertebrae to be stabilized. The sleeve may be moved to facilitate positioning of instruments and/or to facilitate access to the adjacent vertebra that is to be stabilized. For example, the sleeve may be tilted towards the adjacent pedicle so that additional length of an opening in the patient is not needed. The channel in the sleeve may be turned toward the adjacent pedicle that is to be stabilized with the spinal stabilization system being formed. In some embodiments, once resilient insert 106 is positioned on bone fastener 108, cylindrical body 112 may be positioned over resilient insert 106. In some embodiments, cylindrical body 112 may be advanced onto resilient insert 106 to inhibit cylindrical body 112 from moving relative to resilient insert 106. Inhibiting movement may include rotation of cylindrical body 112 about resilient insert 106 and may include cylindrical body 112 withdrawing from resilient insert 106.

A plane of dilated tissue may be created between a first pedicle and a second pedicle to be stabilized with a spinal stabilization system. A first bone fastener assembly 102 and a sleeve may be coupled to the first pedicle. The second pedicle may be adjacent to the first pedicle. In one embodiment, a tissue wedge may be placed in the sleeve coupled to the first pedicle such that the distal end of the tissue wedge contacts the head of the bone fastener. The proximal end of the sleeve coupled to the first pedicle may be held such that tissue around the incision is not pulled or stretched. The tissue wedge may be wanded through the channel in the sleeve and recessed portions 150 in cylindrical body 112 toward the target location at the second pedicle, thereby creating a plane in muscle and other tissue between the head 118 of the installed bone fastener 108 and the target location of a second bone fastener 108. In some embodiments, a tissue wedge may be pivoted about an inside proximal edge of the sleeve such that the distal end of the tissue wedge bluntly splits the muscle and fascia along fibers and create a tissue plane between the two pedicles. The wanding action may be repeated more than once (e.g., two or three times) to create a good working plane and displace unwanted tissue from the plane. The wending may create a tissue plane. In some embodiments, the tissue plane may be substantially trapezoidal. In some embodiments, a tissue plane may be created before bone fastener assembly 102 is inserted into a vertebra.

A tissue plane may be made in a variety of shapes including, but not limited to, substantially trapezoidal, substantially rhomboidal, and substantially triangular. A tissue plane with a substantially geometric shape may have the basic geometric shape with, for example, slightly curved edges and/or slightly rounded corners or apices. In some embodiments, a sleeve length may be chosen to reduce a size of a tissue plane that needs to be formed between pedicles. In some embodiments, creating a trapezoidal tissue plane may reduce the invasiveness of a procedure. Limiting the area of the plane may promote a faster recovery time and/or may reduce an amount of post-operative pain experienced by the patient.

In one embodiment, a tissue wedge may be coupled to a portion of a sleeve to facilitate creation of a tissue plane. In one embodiment, two pedicles may be targeted and bone fastener assemblies 102 may be anchored in both pedicles before creation of a tissue plane. A tissue wedge may be inserted at either of the pedicles. In some embodiments, the sleeves may be coupled to each other at proximal ends of the sleeves. The tissue wedge may be coupled to a sleeve and the sleeve may be used as an anchor during wanding. Insertion of a rod into cylindrical bodies 112 of bone fastener assemblies 102, however, may require cutting of some tissue between the two sleeves. Other procedures may be used to create a tissue plane. For example, before targeting pedicle locations (i.e., before bone fastener insertion), a tissue wedge may be worked downward from an incision to create a tissue plane. Alternatively, a scalpel may be used to cut from the surface of the body to vertebral bone. Extensive use of a scalpel, however, may remove benefits of a minimally invasive procedure.

In one embodiment, a targeting needle may be passed through the tissue to create a tissue plane for insertion of rod 104. Once a well-defined tissue plane has been formed, a targeting needle may be passed down a first sleeve coupled to a first vertebra and then wanded along the formed plane over to a target location at a second pedicle. The target location at the second pedicle may be fluoroscopically confirmed. Bone fastener assembly 102 coupled to a sleeve may be secured in the second pedicle using a procedure similar to the procedure used to insert bone fastener assembly 102 in a first pedicle.

With bone fastener assemblies 102 secured in the vertebral bodies, sleeves coupled to bone fastener assemblies 102 may be oriented to facilitate insertion of rod 104 in the sleeves. In some embodiments, sleeves may serve as tissue retractors during a spinal stabilization procedure. Angular motion of a cylindrical body may be limited by a range of motion allowed between the cylindrical body and the bone fastener to which the cylindrical body is anchored. Angular motion of a cylindrical body may be limited by patient anatomy. Angular motion or orientation of one cylindrical body or sleeve, however, may not depend upon a position of another cylindrical body or sleeve. In some embodiments, channel openings in the sleeves may face each other. In some embodiments, channel openings in the sleeves may be angled relative to each other in various arrangements. A distance between the sleeves may be estimated using an estimating tool. The distance between the sleeves may be used to select a length of rod 104 needed to couple cylindrical bodies 112.

In one embodiment, flexible arms of an estimating tool may be positioned in sleeves. With the activator disengaged, the estimating tool may be advanced toward the pedicles until the arms or members rest on cylindrical bodies 112 or bone fasteners 108 of bone fastener assemblies 102. The activator may be engaged. When the arms are withdrawn from the sleeves, a biasing element may allow the arms to extend to the length indicative of the distance between bone fastener assemblies 102. A length of rod 104 may be selected by measuring a distance between the members of the estimating tool. The measured distance may be increased by an amount to allow rod 104 to extend beyond cylindrical bodies 112 after curvature and/or insertion. In one embodiment, about 5 mm to about 30 mm (e.g., about 15 mm) may be added to the measured distance. In some embodiments, a desired length of rod 104 may be a length that allows rod 104 to extend from each cylindrical body 112 by about 2 mm or about 3 mm. In some embodiments, ends of rod 104 may be flush with the outer surface of one or more cylindrical bodies 112.

In one embodiment, rod 104 of desired length may be chosen by estimating a distance between the sleeves without the use of an estimating tool. The sleeves may be positioned as desired (e.g., substantially parallel to each other). A distance between the most distant outer edges of the sleeves may be estimated. The estimated distance may be increased by an amount to allow rod 104 to extend beyond cylindrical bodies 112 after insertion. In some embodiments, from about 1 mm to about 20 mm may be added to the estimated distance. In some embodiments, a desired length of rod 104 may be a length that allows rod 104 to extend from each cylindrical body 112 by about 2 mm.

Rod 104 may be cut to length and contoured as desired. For example, a medical practitioner may use experience and judgment to determine curvature of a rod for a patient. A desired curvature for rod 104 may be determined using fluoroscopic imaging. In some embodiments, a curvature of rod 104 may be chosen such that, when rod 104 is secured to cylindrical bodies 112 of bone fastener assemblies 102, sleeves coupled to bone fastener assemblies 102 cross at a surface of the skin. Crossing of the sleeves at a surface of the skin allows the medical practitioner to minimize trauma to a patient by minimizing incision length and tissue plane area. Rod 104 may be bent or shaped with a tool (e.g., a rod bender) to allow insertion of rod 104 through channels of sleeves with various spatial locations and/or various angular orientations.

Rods 104 may have shapes including, but not limited to, straight, bent, curved, s-shaped, and z-shaped. In some embodiments, rods 104 may have a substantially circular longitudinal cross section. In some embodiments, rods 104 may have other cross-sectional shapes including, but not limited to, regular shapes (oval, rectangular, rhomboidal, square) and irregular shapes. An instrumentation kit for a spinal stabilization system may include straight rods 104 and/or pre-shaped rods 104. Straight rods 104 and/or pre-shaped rods 104 may be contoured to accommodate patient anatomy if needed during the surgical procedure.

Channels of the sleeves and recessed portions 150 of cylindrical bodies 112 may be oriented by rotating the sleeves to accommodate insertion and seating of rod 104. In some embodiments, a channel opening in a sleeve may be non-linear (e.g., bent, curved, or angled) to allow portions of the spine to be selectively stabilized. Sleeve orientation and/or design may be chosen to allow compression, distraction, and/or reduction of vertebrae. In some embodiments, there may be no constraints governing relative location and/or orientation of the sleeves. Sleeves may be forced apart or angled toward each other or away from each other to accommodate insertion of rod 104.

Prior to insertion of rod 104, the tissue wedge or targeting needle may be used to wand between bone fasteners 108 to ensure a clean plane between bone fasteners 108. An end of rod 104 may be inserted at an angle or substantially longitudinally in a passage and/or channel of a sleeve coupled to bone fastener assembly 102. Inserting rod 104 at an angle or substantially longitudinally allows the length of the incision and/or the area of the tissue plane to remain advantageously small. In some embodiments, sleeves coupled to anchored bone fastener assemblies may remain essentially unconstrained relative to each other during insertion of rod 104. In some embodiments, angular orientation of cylindrical bodies 112 may determine a trajectory of the rod down the sleeves and into cylindrical bodies 112 of bone fastener assemblies 102. Inserting rod 104 down two or more sleeves and through an open path (i.e., the tissue plane) may allow a medical practitioner to avoid surgical difficulties associated with anatomical abnormalities and/or misalignment of system components (e.g., in multi-level stabilization procedures).

Insertion of rod 104 may not be visualized subcutaneously. Therefore, a positioning tool may be used to guide rod 104 down the sleeves into channels 151 in resilient inserts 106 positioned in cylindrical bodies 112. A distal portion of the positioning tool may be contoured. The contour may allow for some rotation of rod 104. With slight pressure, rod 104 may be rotated subcutaneously into a substantially horizontal position and seated in resilient inserts 106. The positioning tool may be held firmly while still allowing a rocking movement between rod 104 and the distal end of the positioning tool. Movement of rod 104 may allow rod 104 to be maneuvered down the sleeves and into resilient inserts 106.

Recessed portions 150 in resilient inserts 106 in cylindrical bodies 112 may be aligned with channels of sleeves to allow rod 104 to be positioned in resilient inserts 106 positioned in cylindrical bodies 112. A positioning tool may be used to angle rod 104 through recessed portions 150 such that an end of rod 104 protrudes through cylindrical body 112. With one end of rod 104 extending through first recessed portions 150 in a first cylindrical body 112, the positioning tool may be used to seat the second end of rod 104 in a second cylindrical body 112 and translate rod 104 to a desired location relative to cylindrical bodies 112. The distal end of the positioning tool inner shaft may be contoured (e.g., curved and/or grooved) to allow some motion (e.g., rocking) of rod 104 while rod 104 is coaxed into position and/or rotated subcutaneously with the positioning tool. Pressure may be applied to the inner shaft to seat rod 104 in recessed portions 150 of cylindrical bodies 112.

In some embodiments, a seater may be used to seat rod 104 in the cylindrical bodies. In some embodiments, a seater may be used to push rod 104 into slots 151 in resilient inserts 106 while the positioning tool is used to maneuver rod 104 into place. Once rod 104 is positioned in resilient inserts 106, fluoroscopic confirmation may ensure that rod 104 is inserted fully into each resilient inserts 106. Prior to securing rod 104 in cylindrical bodies 112 with resilient inserts 106, rod 104 may be gripped firmly with the positioning tool and persuaded cephalad or caudad as needed. With rod 104 seated in resilient inserts 106, orientation of the sleeves may be constrained relative to each other.

In some embodiments, after rod 104 is seated in resilient insert 106, resilient insert 106 may be advanced into cylindrical body 112. Advancing resilient insert 106 into cylindrical body 112 may be performed by advancing rod 104 into resilient insert 106 to seat rod 104 and then continuing to advance rod 104 to advance resilient insert 106 into cylindrical body 112. In some embodiments, after rod 104 is seated in resilient insert 106, the surgeon may seat rod 104 in other resilient inserts before advancing resilient insert 106. Seating rod 104 in multiple resilient inserts 106 in multiple cylindrical bodies 112 before advancing any of the resilient inserts 106 allows a surgeon to verify placement or positioning of rod 104, cylindrical bodies 112 and resilient inserts 106. The surgeon may remove rod 104 from resilient inserts 106, move rod 104 relative to one or more resilient inserts 106, bend rod 104, or make other adjustments or changes to spine stabilization system 100. In some embodiments, after rod 104 is seated in resilient insert 106 and in cylindrical body 112, additional fluoroscopic confirmation of elongated member positioning may be obtained. With the rod satisfactorily positioned, the rod may be secured in place with inserts. After resilient insert 106 is successfully advanced in passage 152 of cylindrical body 112, the tool may be removed from the patient.

Embodiments disclosed herein may be assembled or coupled to bone fasteners without the application of torques. Torque on the pedicle or other portions of the spine may fracture or otherwise damage the spine. In some embodiments, once bone fastener 108 is positioned in a vertebral body, all assembly, coupling, uncoupling, and disassembly may be accomplished using only longitudinal tensile and compressive forces (i.e., pushing and pulling).

Embodiments of spine stabilization system 100 may be used to stabilize two or more vertebral levels (i.e., at least three adjacent vertebrae). In one embodiment, an incision may be made in the skin between the outermost vertebrae to be stabilized. A first bone fastener assembly may be coupled to a first sleeve. The first bone fastener may be threaded into a first pedicle at a target location such that the first sleeve extends above the body surface. The first sleeve may rotate about the head of the first bone fastener. A tissue plane may be created between a channel opening in the first sleeve and a target location at a second pedicle. In one embodiment, the second pedicle may be adjacent to the first pedicle. A second bone fastener assembly may be coupled to a second sleeve and threaded into the second pedicle through the incision. Another tissue plane may be created between the first sleeve or the second sleeve and a target location in a third pedicle. The third pedicle may be adjacent to the first pedicle and/or the second pedicle. A third bone fastener assembly may be coupled to a third sleeve and threaded into the third pedicle through the incision. In one embodiment of a method for a two-level spinal stabilization procedure, an incision may be made above a target location in a middle pedicle. A first bone fastener may be anchored to the middle pedicle. After the first bone fastener is secured, second and third bone fasteners may be coupled to outer pedicles as desired by pulling and/or stretching tissue surrounding the incision to allow access to the outer pedicles.

In some embodiments, spinal stabilization system 100 may be inserted using an invasive procedure. Since insertion of spinal stabilization system 100 in an invasive procedure may be visualized, cannulated components, such as bone fasteners 108 or inserts 106 and/or instruments (e.g., sleeves) may not be needed for the invasive (i.e., open) procedure. Thus, bone fastener 108 used in an invasive procedure may differ from bone fastener 108 used in a minimally invasive procedure.

In some embodiments, tools used in an invasive procedure may be similar to tools used in a minimally invasive procedure. In some embodiments, methods of installing spinal stabilization system 100 in an invasive procedure may be similar to methods of installing spinal stabilization system 100 in a minimally invasive procedure.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the disclosure. It is to be understood that the forms of the disclosure shown and described herein are to be taken as the presently preferred embodiments. Elements and materials may be substituted for those illustrated and described herein, parts and processes may be reversed, and certain features of the disclosure may be utilized independently, all as would be apparent to one skilled in the art after having the benefit of this description of the disclosure. Changes may be made in the elements described herein without departing from the spirit and scope of the disclosure as described in the following claims.

What is claimed is:

1. An apparatus for anchoring a rod to a bone fastener, comprising:
    a first resilient insert comprising:
        a first set of two deflectable arms; and
        a first channel formed between the first set of two deflectable arms;
    a second resilient insert insertable independent from the first resilient insert, the second resilient insert comprising:
        a second set of two deflectable arms; and
        a second channel formed between the second set of two deflectable arms; and
    a cylindrical body having a passage between a first end and a second end thereof, wherein the passage in the cylindrical body has an inner diameter,
    wherein the second end of the cylindrical body comprises two recessed portions, wherein each recessed portion has an associated width greater than the diameter of the rod;
    wherein the first resilient insert has a width greater than the inner diameter of the cylindrical body when the first resilient insert is in a neutral state,
    wherein advancement of the first resilient insert into the passage in the cylindrical body deflects the first set of two deflectable arms inward, causing the width of the first channel to decrease, thereby holding the rod at the first end of the cylindrical body and inhibiting the first resilient insert from moving relative to the cylindrical body, and
    wherein the second resilient insert has a width greater than the inner diameter of the cylindrical body when the second resilient insert is in a neutral state, wherein advancement of the second resilient insert into the passage in the cylindrical body deflects the second set of two deflectable arms inward, causing the width of the second channel to decrease, thereby holding the bone fastener at the second end of the cylindrical body and inhibiting the second resilient insert from moving relative to the cylindrical body.

2. The apparatus of claim 1, wherein at least one of the first set of two deflectable arms and the second set of the two deflectable arms comprise beveled surfaces proximate the first channel or the second channel.

3. The apparatus of claim 1, wherein at least one of the first set of two deflectable arms and the second set of the two deflectable arms comprise radiused surfaces proximate the first channel or the second channel.

4. The apparatus of claim 1, wherein the first channel in the first resilient insert comprises a first slot, wherein compression of the first slot deflects the first set of two deflectable arms inward to decrease the width of the first channel.

5. The apparatus of claim 1, wherein the second channel in the second resilient insert comprises a second slot, wherein compression of the second slot deflects the second set of two deflectable arms inward to decrease the width of the second channel.

6. The apparatus of claim 1, wherein at least one of the first resilient insert and the second resilient insert is cannulated.

7. A system for stabilizing a portion of a spine, comprising:
a rod having a substantially circular cross-sectional geometry;
two or more bone fasteners, wherein each bone fastener comprises:
a threaded shank; and
a head connected to the threaded shank and having an associated diameter; and
two or more anchor assemblies, wherein each anchor assembly comprises:
a first resilient insert comprising:
a first set of two deflectable arms; and
a first channel formed between the first set of two deflectable arms;
a second resilient insert insertable independent from the first resilient insert, the second resilient insert comprising:
a second set of two deflectable arms; and
a second channel formed between the second set of two deflectable arms; and
a cylindrical body having a passage between a first end and a second end thereof,
wherein the passage in the cylindrical body has an inner diameter, wherein the first resilient insert has a width greater than the inner diameter of the cylindrical body when the first resilient insert is in a neutral state, wherein advancement of the first resilient insert into the passage in the cylindrical body deflects the first set of two deflectable arms inward, causing the width of the first channel to decrease, thereby holding the rod at the first end of the cylindrical body and inhibiting the first resilient insert from moving relative to the cylindrical body, and wherein the second resilient insert has a width greater than the inner diameter of the cylindrical body when the second resilient insert is in a neutral state, wherein advancement of the second resilient insert into the passage in the cylindrical body deflects the second set of two deflectable arms inward, causing the width of the second channel to decrease, thereby holding the bone fastener at the second end of the cylindrical body and inhibiting the second resilient insert from moving relative to the cylindrical body.

8. The system of claim 7, wherein at least one of the first set of two deflectable arms and the second set of the two deflectable arms comprise beveled surfaces proximate the first channel or the second channel.

9. The system of claim 7, wherein at least one of the first set of two deflectable arms and the second set of the two deflectable arms comprise radiused surfaces proximate the first channel or the second channel.

10. The system of claim 7, wherein the second end of the cylindrical body comprises two recessed portions, wherein each recessed portion has an associated width greater than or equal to the diameter of the rod.

11. The system of claim 7, wherein the first channel in the first resilient insert comprises a first slot, wherein compression of the first slot deflects the first set of two deflectable arms inward to decrease the width of the first channel.

12. The system of claim 7, wherein the second channel in the second resilient insert comprises a second slot, wherein compression of the second slot deflects the second set of two deflectable arms inward to decrease the width of the second channel.

13. A method for coupling a rod to a portion of the spine, comprising:
advancing a bone fastener into a vertebral body, wherein the bone fastener comprises: a head having an associated diameter; and a threaded shank connected to the head;
advancing a first resilient insert onto the head of the bone fastener, wherein the first resilient insert comprises:
a first set of two deflectable arms; and
a first channel formed between the first set of two deflectable arms, wherein a width of the first channel of the first resilient insert is greater than the diameter of the head of the bone fastener when the first resilient insert is in a neutral state;
positioning a passage at a first end of a cylindrical body over an end of the first resilient insert opposite the first set of two deflectable arms;
positioning a second resilient insert in the passage at a second end of the cylindrical body, wherein the second resilient insert comprises:
a second set of two deflectable arms; and
a second channel formed between the second set of two deflectable arms, wherein a width of the second channel of the second resilient insert is greater than the diameter of a rod when the second resilient insert is in a neutral state;
positioning a portion of a rod in the second channel in the second resilient insert;
and
advancing the first resilient insert and the second resilient insert into the passage in the cylindrical body, wherein a width of the first resilient insert is greater than the inner diameter of the passage of the cylindrical body, wherein advancing the first resilient insert into the passage in the cylindrical body deflects the first set of two deflectable arms inward, causing the width of the first channel to decrease and inhibiting the bone fastener positioned in the first channel of the first resilient insert from moving relative to the first resilient insert, wherein a width of the second resilient insert is greater than the inner diameter of the passage of the cylindrical body, and wherein advancing the second resilient insert into the passage in the cylindrical body deflects the second set of two deflectable arms inward, causing the width of the second channel to decrease and inhibiting the rod positioned in the second channel of the second resilient insert from moving relative to the second resilient insert.

14. The method of claim 13, wherein at least one of the first set of two deflectable arms and the second set of the two deflectable arms comprise beveled surfaces proximate the first channel or the second channel.

15. The method of claim 13, wherein at least one of the first set of two deflectable arms and the second set of the two deflectable arms comprise radiused surfaces proximate the first channel or the second channel.

16. The method of claim 13, wherein the second end of the cylindrical body comprises two recessed portions, wherein each recessed portion has an associated width greater than the diameter of the rod.

17. The method of claim 13, wherein at least one of the first set of two deflectable arms and the second set of two deflectable arms has a first width and a second width that is greater than the first width, wherein advancing the first resilient insert into the cylindrical body comprises advancing the first resilient insert until the first width thereof contacts interior walls of the second end of the cylindrical body and the second width thereof is compressed against the interior walls of the second end of the cylindrical body, and wherein advancing the second resilient insert into the cylindrical body comprises advancing the second resilient insert until the first width thereof contacts interior walls of the second end of the cylindrical body and the second width thereof is compressed against the interior walls of the second end of the cylindrical body.

18. The method of claim 13, wherein the channel in each resilient insert comprises a slot, wherein compression of the slot deflects the two deflectable arms inward.

19. The method of claim 13, wherein one or more steps are performed using Minimally Invasive Surgery (MIS) procedures.

20. The method of claim 19, wherein at least one of the two resilient inserts is cannulated.

\* \* \* \* \*

UNITED STATES PATENT AND TRADEMARK OFFICE
CERTIFICATE OF CORRECTION

PATENT NO.        : 8,197,512 B1                                    Page 1 of 1
APPLICATION NO.   : 12/174484
DATED             : June 12, 2012
INVENTOR(S)       : Wesley Hunt et al.

It is certified that error appears in the above-identified patent and that said Letters Patent is hereby corrected as shown below:

Column 28
Line 22, delete "wending", and insert therefore -- wanding --.

Signed and Sealed this
Twenty-fourth Day of July, 2012

David J. Kappos
*Director of the United States Patent and Trademark Office*